United States Patent
Shih et al.

(10) Patent No.: US 10,124,012 B2
(45) Date of Patent: Nov. 13, 2018

(54) METHOD FOR TREATMENT OF HYPERGLYCEMIA AND HYPERLIPIDEMIA

(71) Applicant: Chun-Ching Shih, Taichung (TW)

(72) Inventors: Chun-Ching Shih, Taichung (TW);
Yueh-Hsiung Kuo, Taichung (TW);
Cheng-Hsiu Lin, Taichung (TW);
Chang-Syun Yang, Taichung (TW)

(73) Assignee: Chun-Ching Shih, Taichung City (TW)

( * ) Notice: Subject to any disclaimer, the term of this patent is extended or adjusted under 35 U.S.C. 154(b) by 0 days.

(21) Appl. No.: 15/587,954

(22) Filed: May 5, 2017

(65) Prior Publication Data

US 2017/0368077 A1 Dec. 28, 2017

(30) Foreign Application Priority Data

Jun. 24, 2016 (TW) .............................. 105119842 A

(51) Int. Cl.
*A61K 31/575* (2006.01)
*A61K 36/07* (2006.01)
*A61P 3/00* (2006.01)

(52) U.S. Cl.
CPC ............ *A61K 31/575* (2013.01); *A61K 36/07* (2013.01); *A61P 3/00* (2018.01)

(58) Field of Classification Search
CPC .................................................. A61K 31/575
See application file for complete search history.

(56) References Cited

PUBLICATIONS

Kuo et al., Evid. Based Complement Alternat. Med., published online May 8, 2016.*
Yueh-Hsiung Kuo et al., "Antcin K, a Triterpenoid Compound from *Antrodia* camphorata, Displays Antidiabetic and Antihyperlipidemic Effects via Glucose Transporter 4 and AMP-Activated Protein Kinase Phosphorylation in Muscles", Evidence-Based Complementary and Alternative Medicine, vol. 2016, Article ID 4867092, 16 pages.
Yueh-Hsiung Kuo et al., "Dehydroeburicoic Acid from Antrodia camphorate Prevents the Diabetic and Dyslipidemic State via Modulation of Glucose Transporter 4, Peroxisome Proliferator-Activated Receptor α Expression and AMP-Activated Protein Kinase Phosphorylation in High-Fat-Fed Mice", Int. J. Mol. Sci. 2016, 17, 872, 19 pages.

* cited by examiner

*Primary Examiner* — Svetlana M Ivanova
(74) *Attorney, Agent, or Firm* — Wang Law Firm, Inc.

(57) ABSTRACT

Provided is a method of treating metabolic diseases including type 2 diabetes, insulin resistance, hyperglycemia, hyperlipidemia, obesity, hepatic steatosis, and hyperinsulinemia in a subject in need, including the step of administering to the subject a therapeutically effective amount of antcin K. Also provided is a method of enhancing protein expression ratio of phospho-5' adenosine monophosphate-activated protein kinase (phospho-AMPK) to total AMPK in skeletal muscle or liver of a subject, and a method of reducing blood leptin in a subject. Antcin K exerts prominent antidiabetic and antihyperlipidemic effects through regulation of membrane GLUT4, AMPK, Akt PPARα, FAS, and PPARγ protein expressions and G6Pase, DGAT2, SREBP-1c, aP2, apoCIII, SREBP2, and PPARα mRNA expressions.

13 Claims, 15 Drawing Sheets

Specification includes a Sequence Listing.

SEQUENCE LISTING

<160> NUMBER OF SEQ ID NOS: 16

<210> SEQ ID NO 1
<211> LENGTH: 22
<212> TYPE: DNA
<213> ORGANISM: Artificial sequence
<220> FEATURE:
<223> OTHER INFORMATION: PCR primer

<400> SEQUENCE: 1
gaacaactaa agcctctgaa ac                                          22

<210> SEQ ID NO 2
<211> LENGTH: 22
<212> TYPE: DNA
<213> ORGANISM: Artificial sequence
<220> FEATURE:
<223> OTHER INFORMATION: PCR primer

<400> SEQUENCE: 2
ttgctcgata cataaaacac tc                                          22

<210> SEQ ID NO 3
<211> LENGTH: 20
<212> TYPE: DNA
<213> ORGANISM: Artificial sequence
<220> FEATURE:
<223> OTHER INFORMATION: PCR primer

<400> SEQUENCE: 3
ggctgttgtc taccataagc                                             20

<210> SEQ ID NO 4
<211> LENGTH: 20
<212> TYPE: DNA
<213> ORGANISM: Artificial sequence
<220> FEATURE:
<223> OTHER INFORMATION: PCR primer

<400> SEQUENCE: 4
aggaagaaac gtgtcaagaa                                             20

<210> SEQ ID NO 5
<211> LENGTH: 23
<212> TYPE: DNA
<213> ORGANISM: Artificial sequence
<220> FEATURE:
<223> OTHER INFORMATION: PCR primer

<400> SEQUENCE: 5
agtggcaatg ctatcatcat cgt                                         23

<210> SEQ ID NO 6
<211> LENGTH: 24
<212> TYPE: DNA
<213> ORGANISM: Artificial sequence
<220> FEATURE:
<223> OTHER INFORMATION: PCR primer

<400> SEQUENCE: 6
aaggaataag tgggaaccag atca                                        24

<210> SEQ ID NO 7
<211> LENGTH: 20
<212> TYPE: DNA
<213> ORGANISM: Artificial sequence

```
<220> FEATURE:
<223> OTHER INFORMATION: PCR primer

<400> SEQUENCE: 7
cagttttatc cctagaagca                                               20

<210> SEQ ID NO 8
<211> LENGTH: 19
<212> TYPE: DNA
<213> ORGANISM: Artificial sequence
<220> FEATURE:
<223> OTHER INFORMATION: PCR primer

<400> SEQUENCE: 8
tctcacgact caatagctg                                                19

<210> SEQ ID NO 9
<211> LENGTH: 20
<212> TYPE: DNA
<213> ORGANISM: Artificial sequence
<220> FEATURE:
<223> OTHER INFORMATION: PCR primer

<400> SEQUENCE: 9
atatcattga aaagcgctac                                               20

<210> SEQ ID NO 10
<211> LENGTH: 20
<212> TYPE: DNA
<213> ORGANISM: Artificial sequence
<220> FEATURE:
<223> OTHER INFORMATION: PCR primer

<400> SEQUENCE: 10
attttcaagt ccacatcact                                               20

<210> SEQ ID NO 11
<211> LENGTH: 20
<212> TYPE: DNA
<213> ORGANISM: Artificial sequence
<220> FEATURE:
<223> OTHER INFORMATION: PCR primer

<400> SEQUENCE: 11
acctctgttc atgtcagacc                                               20

<210> SEQ ID NO 12
<211> LENGTH: 20
<212> TYPE: DNA
<213> ORGANISM: Artificial sequence
<220> FEATURE:
<223> OTHER INFORMATION: PCR primer

<400> SEQUENCE: 12
ataaccacag accaaccaag                                               20

<210> SEQ ID NO 13
<211> LENGTH: 20
<212> TYPE: DNA
<213> ORGANISM: Artificial sequence
<220> FEATURE:
<223> OTHER INFORMATION: PCR primer

<400> SEQUENCE: 13
tcacctggaa gacagctcct                                               20
```

```
<210> SEQ ID NO 14
<211> LENGTH: 19
<212> TYPE: DNA
<213> ORGANISM: Artificial sequence
<220> FEATURE:
<223> OTHER INFORMATION: PCR primer

<400> SEQUENCE: 14
tgcctgccac tttccttgt                                                  19

<210> SEQ ID NO 15
<211> LENGTH: 20
<212> TYPE: DNA
<213> ORGANISM: Artificial sequence
<220> FEATURE:
<223> OTHER INFORMATION: PCR primer

<400> SEQUENCE: 15
tgtgtccgtc gtggatctga                                                 20

<210> SEQ ID NO 16
<211> LENGTH: 21
<212> TYPE: DNA
<213> ORGANISM: Artificial sequence
<220> FEATURE:
<223> OTHER INFORMATION: PCR primer

<400> SEQUENCE: 16
cctgcttcac caccttcttg a                                               21
```

METHOD FOR TREATMENT OF HYPERGLYCEMIA AND HYPERLIPIDEMIA

CROSS-REFERENCE TO RELATED APPLICATION

This application claims priority of Taiwan Patent Application No. 105119842, filed on Jun. 24, 2016, the content of which is incorporated herein in its entirety by reference.

BACKGROUND OF THE INVENTION

1. Field of the Invention

The present invention relates to a method of treating hyperglycemia, hyperlipidemia, and hepatic steatosis. Particularly, the present invention relates to a method of treating hyperglycemia, hyperlipidemia, and hepatic steatosis with antcin K isolated from *Antrodia camphorata* fruiting bodies.

2. The Prior Art

Diabetes mellitus hardly occurs in isolation but is most often a part of an array of metabolic abnormalities that includes insulin resistance, hyperinsulinemia, and hypertriglyceridemia. Type 2 diabetes is estimated to affect a population of about 300 million people by 2025, and it accounts for more than 90% of all diabetes mellitus. The pathogenesis of type 2 diabetes has been proposed as insulin resistance, which is attributed to insulin insensitivity in adipose tissue, skeletal muscle, or liver tissue and β-cell dysfunction.

The pancreas secretes insulin to maintain normal glucose homeostasis. The elevated glucose levels, after huge caloric intake, are rapidly returned to normal because secreted insulin stimulates glucose uptake via eliciting translocation of glucose transporter type 4 (GLUT4) from intracellular sites to the plasma membrane. Thus, GLUT4 has been regarded as a vital determinant of blood glucose homeostasis. For type 2 diabetic patients, levels of insulin-induced GLUT4 translocation in skeletal muscle of are markedly decreased. Therefore, enhancement of GLUT4 expression and translocation may be the target of drug development.

Glucose uptake from blood into peripheral tissues is promoted by two pathways, including insulin-dependent mechanisms leading to protein kinase B (PKB, also termed Akt) activation and contraction-regulated stimulation or hypoxia-regulated activation of 5' adenosine monophosphate-activated protein kinase (AMPK). AMPK plays a dominant role in glucose and lipid metabolism. Since dysregulation of glucose and lipid metabolism is marked in type 2 diabetes, AMPK activators would be promising therapies.

Metformin is commonly used in the clinics as an antidiabetic drug in the management of type 2 diabetes, and it activates AMPK in both hepatocyte and skeletal muscle. However, it causes side effects of lactic acidosis, vomiting, diarrhea, nausea, vomiting, and flatulence.

Peroxisome proliferator-activated receptor α (PPARα) plays a key role in regulation of lipid metabolism and reduces circulating triglyceride (TG) concentrations via regulating numerous genes associated with lipogenesis and fatty acids oxidation. Fenofibrate, as one of PPARα agonists, has been used in the treatment of hypertriglyceridemia.

The high-fat diet-fed C57BL/6J mouse is a mouse model that is widely used to investigate disease mechanisms of type 2 diabetes and as a tool for developing novel therapeutic interventions, because the mouse could induce early type 2 diabetes, markedly increase adipose weights, produce insulin resistance, and increase blood glucose, total cholesterol (TC), and TG levels.

*Antrodia camphorata* (Polyporaceae, Aphyllophorales) is edible as a folk remedy in the treatment of a variety of diseases in Taiwan. It is rare and expensive because it grows only on the inner heartwood wall of the endemic evergreen *Cinnamomum kanehirai*. The mycelia, filtrate of broth, and fruiting bodies of *A. camphorata* exhibit numerous physiological functions. The fruiting bodies of *A. camphorata* contain terpenoids, such as antcins (A, B, and C), zhankuic acids (A, B, C, D, and E), 15α-acetyl-dehydrosulphurenic acid, dehydroeburicoic acid, dehydrosulphurenic acid, antcins E and F, methyl antcinate G, methyl antcinate H, and eburicoic acid. The solid culture of the fruiting bodies and the filtrate in submerged culture has been shown to have antioxidant activities.

Previous study had demonstrated that, in terms of in vivo metabolism, 13 terpenoids in *A. camphorata* were detected by using LC/MS/MS in rat plasma after oral administration, and plasma concentrations of ergostanoids were much higher than those of lanostanoids. The ergostanoids underwent reduction and hydroxylation reactions in vivo with their mean residence time (MRT) ranged from 3 to 6 hours. The lanostanoids were inactive to metabolic reactions and were slowly eliminated with an MRT of 9~16 hours.

Antcin K ($3\alpha,4\beta,7\beta$-trihydroxy-$4\alpha$-methylergosta-8,24 (28)-dien-11-on-25S-26-oic acid; abbreviated as AnK), an active triterpenoid from the fruiting bodies of basswood cultivated *A. cinnamomea*, is capable of inducing apoptotic cell death in human liver cancer Hep3B cells. Also, antcin K isolated from ethanol extracts of wild fruiting bodies of *A. camphorata* has shown concentration-dependent (1~25 mM) anti-inflammatory effects (by modulation of leukocyte activity and inhibition of reactive oxygen species production) induced by chemotactic substances such as fMLP and TPA in human neutrophils.

Recent studies demonstrated that ergostatrien-3β-ol and dehydroeburicoic acid from *A. camphorata* exhibited excellent antihyperglycemic and antihyperlipidemic activities. Nevertheless, the effects of antcin K, the main constituent of the fruiting body of *A. camphorata,* on diabetes and dyslipidemia are still unknown.

SUMMARY OF THE INVENTION

In one aspect, the present invention provides a method of treating a metabolic disease in a subject in need, including administering to the subject a therapeutically effective amount of antcin K, wherein the metabolic disease is selected from the group consisting of type 2 diabetes, insulin resistance, hyperglycemia, hyperlipidemia, obesity, hepatic steatosis, hyperinsulinemia, and combinations thereof.

In one embodiment of the present invention, the antcin K blood glucose and blood insulin, and increases insulin sensitivity. To reduce blood glucose, the antcin K enhances protein expression of membrane GLUT4 in skeletal muscle and protein expression ratio of phospho-5' adenosine monophosphate-activated protein kinase (also referred to as phospho-AMPK or p-APMK) to total AMPK (also referred to as total-AMPK or t-AMPK) in skeletal muscle and liver, and inhibits mRNA expression of glucose-6-phosphatase (G6Pase). The antcin K also increases phosphorylation of protein kinase B (Akt) in skeletal muscle.

In another embodiment of the present invention, the antcin K reduces triglycerides, total cholesterol, and free fatty acid (FFA) in blood. To reduce blood triglycerides, the antcin K inhibits protein expression of fatty acid synthase (FAS) and mRNA expression of sterol regulatory element-binding protein 1c (SREBP1c) and diacylglycerol O-acyltransferase 2 (DGAT2) in liver. Also, the antcin K enhances PPARα protein expression in liver to promote fatty acid oxidation. Furthermore, the antcin K inhibits mRNA expression of sterol regulatory element-binding protein 2 (SREBP2) to reduce total cholesterol in blood.

In yet another embodiment of the present invention, the antcin K inhibits hepatocellular ballooning or reduces hepatic total lipids and triacylglycerol. More specifically, the antcin K enhances protein expression of PPARα and inhibits protein expression of FAS to reduce hepatic total lipids and triacylglycerol.

In still another embodiment of the present invention, the antcin K inhibits protein expression of FAS and peroxisome proliferator-activated receptor γ (PPARγ) in adipocytes to inhibit adipocyte differentiation and fat accumulation to decrease adipocyte size. Additionally, the antcin K decrease visceral fat mass but increase blood adiponectin to ameliorate the metabolic disease.

In another aspect, the present invention provides a method of enhancing protein expression ratio of phospho-AMPK to total AMPK in skeletal muscle or liver of a subject, including administering to the subject a therapeutically effective amount of the antcin K.

In still another aspect, the present invention provides a method of reducing blood leptin in a subject, including administering to the subject a therapeutically effective amount of antcin K.

Through administration of antcin K isolated from *A. camphorata* extracts, the diseases such as type 2 diabetes induced by high-fat diet (HFD) and the related symptoms can be alleviated and the following effects are achieved.

The blood glucose of HFD-induced diabetic mice is significantly reduced after treatment with antcin K at a dose of 10, 20 or 40 mg/kg body weight/day, indicating that antcin K is effective in treating diabetes. The dose of 10 mg/kg body weight/day for a mouse can be converted to a daily dose of about 52.64 mg for a 70 kg human subject, which is equivalent to about 0.752 mg/kg body weight/day, based on the guideline on estimating the maximum safe starting dose in initial clinical trials for therapeutics in adult healthy volunteers issued by U.S. Food and Drug Administration (FDA) in 2005.

In addition, levels of triglycerides and total cholesterol (TC) in the blood of HFD induced diabetic mice are reduced after treatment with antcin K, indicating that antcin K is effective in improving dyslipidemia.

Treatment of antcin K further enhances expression of GLUT4 and phospho-AMPK in the liver and skeletal muscle of HFD-induced diabetic mice, indicating that antcin K is effective in improving hyperglycemia.

Along with the process of treating hyperglycemia with antcin K, mRNA expression of G6Pase is also decreased, leading to inhibited hepatic gluconeogenesis and ameliorating diabetic conditions.

In one embodiment of the present invention, antcin K treatment reduces blood levels of triglycerides in HFD-induced diabetic mice through inhibiting FAS protein expression.

In one embodiment of the present invention, antcin K treatment reduces blood levels of total cholesterol and SREBP-2 mRNA expression in HFD-induced diabetic mice, showing that antcin K may prevent or ameliorate diabetes and dyslipidemia through increasing protein expression of membrane GLUT4 in skeletal muscle, increasing PPARα protein expression that involves in fatty acid oxidation, decreasing FAS protein expression, and increasing protein expression ratio of phospho-AMPK/total-AMPK.

The present invention is further explained in the following drawings and examples. It is understood that the examples given below do not limit the scope of the invention, and it will be evident to those skilled in the art that modifications can be made without departing from the scope of the appended claims.

BRIEF DESCRIPTION OF THE DRAWINGS

The present invention will be apparent to those skilled in the art from the following detailed description of the preferred embodiments, with reference to the attached drawings, in which.

DETAILED DESCRIPTION OF THE PREFERRED EMBODIMENT

Definition

As used herein, the phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dosage for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts.

Figure 1:
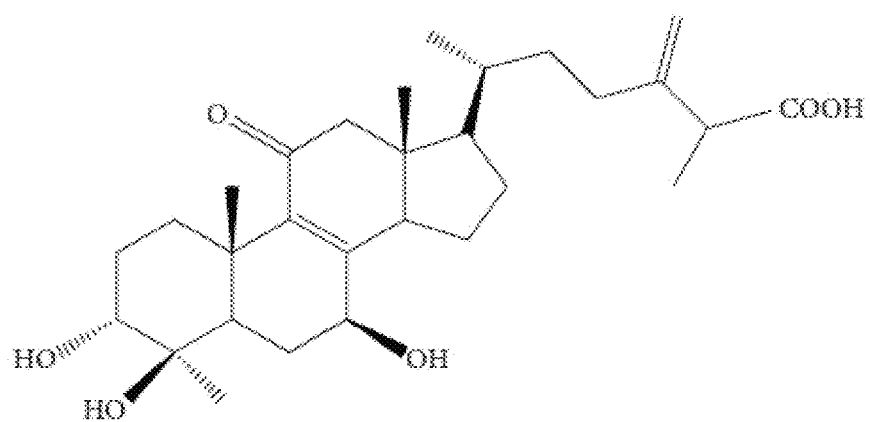
FIG. 1 shows the chemical structure of antcin K (AnK).

The present invention provides a method of treating metabolic diseases including type 2 diabetes, hyperglycemia, hyperlipidemia, and hepatic steatosis in a subject in need. The method includes the step of administering to the subject a therapeutically effective amount of antcin K (AnK), a compound with the chemical structure shown in FIG. 1. In the following embodiments, a screen for evaluating the potential effects of AnK was performed in vitro in myoblasts, followed by further verification of the hypothesis that AnK could display beneficial effects on metabolism in mammals, including reduction in blood glucose, hepatic lipids, and triglycerides and total cholesterol in blood. The effects of AnK were compared with those of the clinical drugs such as metformin and fenofibrate. Moreover, the present invention investigates the influence of AnK on membrane GLUT4 protein expression and AMPK activation via phosphorylation of Thr172 of α subunit. The expressions of target genes were also determined, including PPARα and FAS from the peripheral tissues of HFD-fed mice treated with AnK.

Methods and Materials

Antibodies to GLUT4 (no. sc-79838) were obtained from Santa Cruz Biotech (Santa Cruz, Calif., USA). Antibodies to phospho-AMPK (Thr$^{172}$), PPARα (no. ab8934), and PPARγ (no. ab45036) were purchased from Abcam Inc. (Cambridge, Mass., USA). Antibodies to FAS (no. 3180), phospho-Akt (Ser$^{473}$) (no. 4060), total AMPK (Thr$^{172}$), and β-actin (no. 4970) were purchased from Cell Signaling Technology (Danvers, Mass., USA). Secondary anti-rabbit antibodies were purchased from Jackson ImmunoRes. Lab., Inc. (West Grove, Pa., USA).

Preparation of AnK

The fruiting body of A. camphorata was purchased from the Balay Biotechnology Corporation (Hsinchu City, Taiwan). A voucher specimen (CMPC393) was deposited at and identified by China Medical University. The fruiting bodies of A. camphorata (3.0 kg) were extracted three times with methanol, followed by isolation of AnK via chromatography using 50% ethyl acetate and 50% hexane according to the procedures previously described by Shen et al. ("New ergostane and lanostane from Antrodia camphorata", The Journal of Chinese Medicine, 2003, 14(4), pp. 247-258) The purity of AnK was above 99%. The analysis was performed on a high performance liquid chromatography (HPLC) system (SHIMADZU LC 20-A, Kyoto, Japan) equipped with a TSKgel ODS-80Ts column (TOSOH) and the analytical condition was 100% methanol.

Cell Culture

For the in vitro assay, C2C12 skeletal myoblasts (ATCC CRL-1772) were cultured at 37° C. in Dulbecco's modified Eagle's medium (DMEM; Gibco BRL) supplemented with 10% fetal bovine serum (FBS; Hyclone) and 100 U/ml penicillin and 100 μg/ml streptomycin (Gibco BRL), and split 1:4 using 0.05% trypsin at 80% confluency. Myoblasts were diluted and placed in a 9 cm dish. Cells were cultured to achieve 80-90% confluency and refreshed with growth media (2% FBS/DMEM) every 24 hours for 5-7 days. The term "confluency" refers to the proportion of the surface of a culture dish that is covered by adherent cells growing in the dish. 100% confluency refers to complete coverage of the surface by the cells.

Detection of Expression Levels of Membrane GLUT4 and Akt Phosphorylation in Vitro Differentiated C2C12 cells were serum-starved in DMEM/BSA at 37° C. for 2 hours prior to incubation with AnK (at 1, 5, 10, and 25 μg/mL) or vehicle (0.2% dimethyl sulfoxide (DMSO) in saline) for 30 min or with 100 nM insulin for 25 min.

The abovementioned C2C12 cells were then washed three times with phosphate buffered saline (PBS) and divided into two groups. The C2C12 cells of one group were homogenized in RIPA buffer supplemented with complete protease inhibitor cocktail (Roche) and phosphatase inhibitors, and centrifuged at 20000 g for 20 minutes. The proteins in the supernatant were collected stored at −20° C. The RIPA buffer had a pH value of about 8 and contained 50 mM tris (hydroxymethyl) aminomethane hydrochloride (Tris-HCl), 150 mM sodium chloride, 1% Nonidet P-40, 0.5% sodium deoxycholate, and 0.1% sodium dodecyl sulfate (SDS).

The C2C12 cells of the other group were homogenized in a homogenization buffer having a pH value of about 7.4 and containing 250 mM sucrose, 50 mM Tris, and 0.2 mM edetic acid (EDTA). The homogenates were then centrifuged at 9000 g for 10 minutes at 4° C. The pellet was subjected to three repetition of resuspension with 0.5 mL homogenization buffer and centrifugation. The supernatants from the repeated centrifugation were collected and mixed, followed by a 60-minute centrifugation at 190000 g and at 4° C. The pellet with cell membrane was resuspended with 0.2 mL homogenization buffer and stored at −20° C.

Protein concentrations were determined via BCA assay (Pierce). Equal amounts of proteins were diluted four times in SDS sample buffer, and subjected to SDS polyacrylamide gel electrophoresis (SDS-PAGE) and Western blotting. Proteins were detected with antibodies specific for GLUT4, Akt, phospho-Akt (Ser$^{473}$), AMPK, and phospho-AMPK (Thr$^{172}$).

Animal Study

Animal studies were performed and approved under the guidelines of the Institutional Animal Care and Use Committee in Taiwan (12 Mar. 2015). The 4-week old male C57BL/6J mice (total amount n=63) were obtained from the National Laboratory Animal Center (Taipei, Taiwan). After acclimatization for one week, all of the mice were randomly assigned into a control (CON) group and a high-fat diet (HFD) group. For the following 12 weeks, the CON group (n=9) received a control diet or a low-fat diet (Diet 12450B, Research Diets, Inc., New Brunswick, N.J., USA), while the HFD group (n=54) received a high-fat diet (Diet 12451, Research Diets, New Brunswick, N.J., USA). The low-fat diet was composed of protein 20%, carbohydrate 70% and fat 10%, whereas the high-fat diet was composed of protein 20%, carbohydrate 35%, and fat 45% (of total energy, % kcal). After HFD feeding for 8 weeks, the HFD group was randomly subdivided into six groups (n=9 per group) receiving different treatments and fed on HFD. The six groups were the HF+AnK1 group (dosing of AnK at 10 mg/kg body wt/day), the HF+AnK2 group (dosing of AnK at 20 mg/kg body wt/day), the HF+AnK3 group (dosing of AnK at 40 mg/kg body wt/day), the HF+Metf group (dosing of metformin at 300 mg/kg body weight/day), the HF+Feno group (dosing of fenofibrate (Sigma Chemical Co, St. Louis, Mich., USA) at 250 mg/kg body weight/day), and the HF group which was given vehicle (equal volumes of distilled water). The HF+AnK1, HF+AnK2, and HF+AnK3 groups are collectively termed AnK-treated HFD groups in the following examples. The CON mice were administered vehicle. All treatments were administered via oral gavage once daily. After administration for 4 weeks, all mice were fasted 12 hours, and blood was collected from the retro-orbital sinus under ether anesthesia. At the end of the experiment, the mice were sacrificed via carbon dioxide inhalation. Liver, adipose tissue, and skeletal muscle were collected and immediately stored at −80° C. for target gene analysis.

Measurement of Metabolic Parameters

The metabolic parameters, including body weight, weight gain, and food intake, were performed as the following. Body weight was daily measured at the same time throughout the study. Body weight gain is considered as the weight difference between two consecutive days. The amount of pellet food was weighted, followed by weighting the amount of remaining food after 24 hours. The difference between the two weights is defined as daily food intake.

Measurement of Blood Glucose Levels and Biochemical Parameters

A portion of the blood samples obtained from the retro-orbital sinus of fasted mice were immediately used to measure blood glucose levels using Sidekick glucose analyzer (YSI 1500, YSI Incorporated, Yellow Springs, USA) according to the glucose oxidase method. Heparin (30 units/mL, Sigma) was added into other portions of the blood samples. Plasma samples for the following analysis were prepared from these blood samples via centrifugation at 1600 g for 15 minutes at 4° C., followed by plasma separation within 30 minutes. Blood levels of triglycerides (TG), total cholesterol (TC), and free fatty acids (FFA) were determined using commercial assay kits in accordance with manufacturer's directions (Triglycerides-E test, Cholesterol-E test and FFA-C test, Wako Pure Chemical, Osaka, Japan). Blood levels of insulin, leptin, and adiponectin were measured by enzyme-linked immunosorbent assay (mouse insulin ELISA kit, Mercodia, Uppsala, Sweden; mouse leptin ELISA kit, Morinaga, Yokohama, Japan; mouse adiponectin ELISA kit, Crystal Chem International, Downers Grove, Ill., USA).

Measurement of Hepatic Lipids

For hepatic lipid extraction, liver samples (0.375 g) were homogenized with 1 mL distilled water for 5 minutes. After centrifugation, the dried pellet was finally resuspended in 0.5 mL ethanol and analyzed using a triglyceride kit as used for analyzing the blood lipids set forth above.

Histopathology Examination

Parts of visceral adipose and liver specimens were fixed with formalin (200 g/kg) neutral buffered solution and embedded in paraffin. A series of 8 μm-thick sections was cut and stained with hematoxylin and eosin. For microscopic examination, a microscope (Olympus BX51, Olympus, Tokyo, Japan) was used and the images were photographed.

Isolation of RNA

Total RNA from liver tissue of mice was isolated with a Trizol Reagent (Molecular Research Center, Inc., Cincinnati, Ohio, USA) according to the manufacturer's instructions. The integrity of the extracted total RNA was examined by 2% agarose gel electrophoresis, and the RNA concentration was determined by the ultraviolet (UV) light absorbency at 260 nm and 280 nm (Spectrophotometer U-2800A, Hitachi). The quality of the RNA was confirmed by ethidium bromide staining of 18S and 28S ribosomal RNA after electrophoresis on 2% agarose gel containing 6% formaldehyde.

Relative Quantization of mRNA

Levels of mRNA of target genes were quantified by semi-quantitative reverse transcription polymerase chain reaction (RT-PCR). The isolated total RNA (1 μg) was reverse transcribed to cDNA in a reaction mixture containing buffer, 2.5 mM dNTP (Gibco-BRL, Grand Island, N.Y.), 1 mM oligo (dT) primer, 50 mM dithiothreitol, 40 U Rnase inhibitor (Gibco-BRL, Grand Island, N.Y.), and 5 μL Moloney murine leukemia virus reverse transcriptase (TEpicentre, Madison, Wis., USA) at 37° C. for 1 hour and then heated at 90° C. for 5 minutes to terminate the reaction. The PCR was performed in a final 25 μL containing 1 U Blend Taq-Plus (TOYOBO, Japan), 10 μL of the RT cDNA product, 10 μM of each forward (F) and reverse (R) primer, 75 mM Tris-HCl (pH 8.3) containing 1 mg/L Tween 20, 25 mM dNTP, and 2 mM magnesium chloride. The primers used are shown in TABLE 1. PCR products were analyzed by 2% agarose gel and stained with ethidium bromide. The relative intensity of each band was evaluated using AlphaDigiDoc 1201 software (Alpha Innotech Co., San Leandro, Calif., USA) and normalized to the band intensity of GAPDH in each sample.

TABLE 1

| Primers used in PCR amplification | | | | |
|---|---|---|---|---|
| Gene | Accession number | Forward primer and reverse primer | PCR product (bp) | Annealing temperature (° C.) |
| Liver | | | | |
| G6Pase | NM_008061.3 | F: GAACAACTAAAGCCTCTGAAAC (SEQ ID NO: 1)<br>R: TTGCTCGATACATAAAACACTC (SEQ ID NO: 2) | 350 | 50 |

TABLE 1 -continued

Primers used in PCR amplification

| Gene | Accession number | Forward primer and reverse primer | PCR product (bp) | Annealing temperature (° C.) |
|---|---|---|---|---|
| SREBP1c | NM_011480 | F: GGCTGTTGTCTACCATAAGC (SEQ ID NO: 3)<br>R: AGGAAGAAACGTGTCAAGAA (SEQ ID NO: 4) | 219 | 48 |
| DGAT2 | NM_026384.3 | F: AGTGGCAATGCTATCATCATCGT (SEQ ID NO: 5)<br>R: AAGGAATAAGTGGGAACCAGATCA (SEQ ID NO: 6) | 149 | 50 |
| apo C-III | NM_023114.3 | F: CAGTTTTATCCCTAGAAGCA (SEQ ID NO: 7)<br>R: TCTCACGACTCAATAGCTG (SEQ ID NO: 8) | 349 | 47 |
| SREBP2 | AF289715.2 | F: ATATCATTGAAAAGCGCTAC (SEQ ID NO: 9)<br>R: ATTTTCAAGTCCACATCACT (SEQ ID NO: 10) | 256 | 48 |
| PPARa | NM_011144 | F: ACCTCTGTTCATGTCAGACC (SEQ ID NO: 11)<br>R: ATAACCACAGACCAACCAAG (SEQ ID NO: 12) | 352 | 49 |
| aP2 | NM_024406 | F: TCACCTGGAAGACAGCTCCT (SEQ ID NO: 13)<br>R: TGCCTGCCACTTTCCTTGT (SEQ ID NO: 14) | 142 | 52 |
| GAPDH | NM_007392 | F: TGTGTCCGTCGTGGATCTGA (SEQ ID NO: 15)<br>R: CCTGCTTCACCACCTTCTTGA (SEQ ID NO: 16) | 99 | 55 |

Western Blotting

Protein extraction and immunoblots were carried out for determination of expression levels of muscular membrane GLUT4, muscular and hepatic phospho-AMPK ($Thr^{172}$)/total-AMPK, muscular and hepatic phospho-Akt ($Ser^{473}$)/total-Akt, hepatic PPARα and FAS, and PPARγ and FAS in adipose tissue. About 0.1 g of liver tissue, skeletal muscle, or adipose tissue was used for the homogenate samples. Samples were powdered under liquid nitrogen and homogenized for 20 seconds in 500 μL buffer containing 20 mM Tris-HCl (pH 7.4 at 4° C.), 2% SDS, 5 mM EDTA, 5 mM EGTA, 1 mM dithiothreitol (DTT), 100 mM NaF, 2 mM sodium vanadate, 0.5 mM phenylmethylsulfonyl fluoride, 10 μg/mL leupeptin, and 10 μL/mL pepstatin. The total membrane fraction was used for measurement. The protein concentration in supernatant was determined with a BCA protein assay kit (Thermo Scientific, Rockford, Ill., USA). 20 μg of proteins were separated by electrophoresis on a 12% polyacrylamide gel and transferred to a nitrocellulose membrane. The membrane was blocked with 5% slim milk in Tris-buffered saline (TBS)(Amersham BioSciences, Uppsala, Sweden) containing 0.05% Tween-20 (Bio Rad, CA, USA) and incubated overnight at 4° C. with antibodies at 1:200 dilution. Subsequently, the membrane was washed three times with TBS containing 0.05% Tween-20 and incubated with secondary antibody anti-rabbit (1:1000) (Jackson ImmunoResearch Laboratories, Inc., PA, USA) for 1 hour. Immunoreactive bands were detected with ECL reagent kit (GE Healthcare BioSciences, Buckinghamshire, UK). The intensity of Western blot signals was analyzed using AlphaEase FC software (Alpha Innotech Corporation, Randburg, South Africa). The structural protein GAPDH in the samples was used as the loading control.

Statistics

Results are presented as the means±standard errors (SE). Comparisons between groups were performed using ANOVA and coupled with Dunnett's tests. P values less than 0.05 were considered statistically significant.

EXAMPLE 1

AnK Enhances Expression Levels of Membrane GLUT4 and Akt Phosphorylation

To evaluate the antidiabetic potential of AnK, C2C12 myoblast cells without treatment (the control group) or treated with insulin, DMSO, or various amounts of AnK were examined for expression levels of membrane GLUT4, phospho-Akt ($Ser^{473}$)/total-Akt, and phospho-AMPK ($Thr^{172}$)/total-AMPK.

Figure 2A:
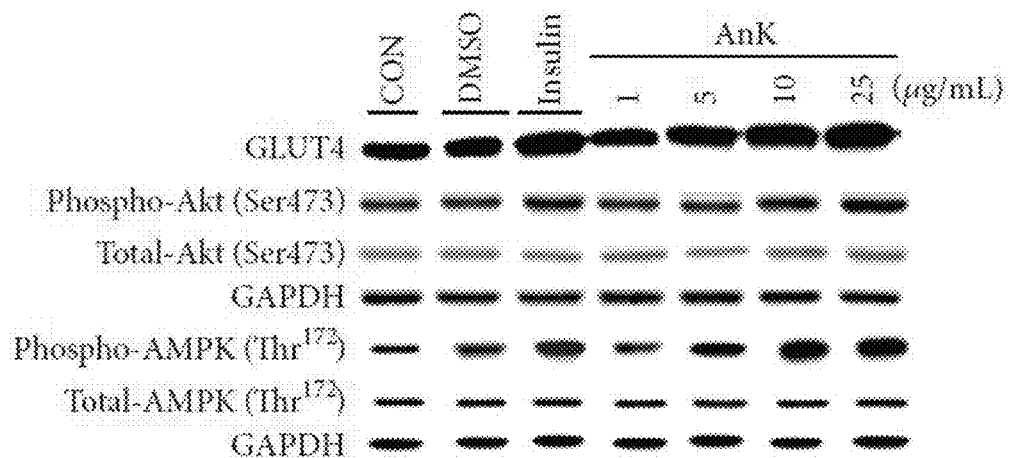
FIG. 2A shows Western blotting images of membrane GLUT4, phospho-protein kinase B (often termed phospho-Akt), total-Akt, phospho-AMPK, and total-AMPK, in C2C12 myoblast cells without treatments (referred to as CON) or treated with DMSO, insulin, or various amounts of AnK (1, 5, 10 and 25 µg/mL)
Figure 2B:
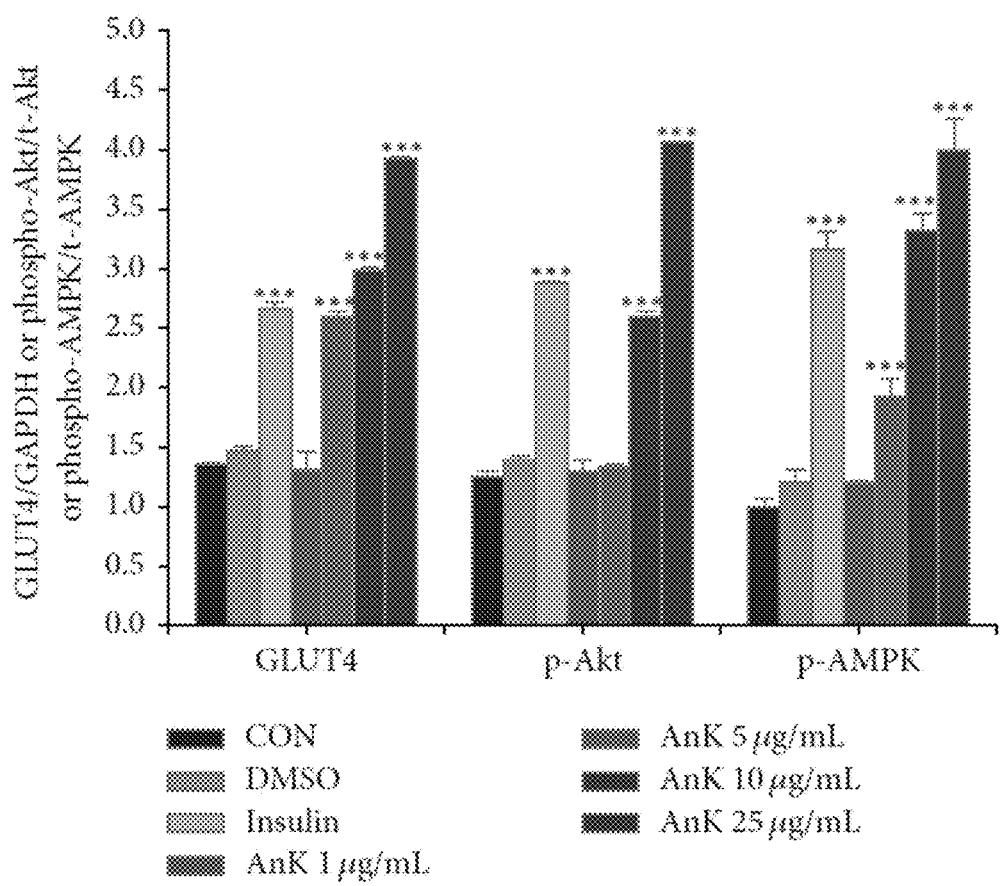
FIG. 2B shows quantification of protein expression levels of membrane GLUT4, normalized to glyceraldehyde 3-phosphate dehydrogenase (GAPDH) levels, the ratio of phospho-Akt ($Ser^{473}$) to total-Akt (t-Akt), and the ratio of phospho-AMPK ($Thr^{172}$) to total-AMPK (t-AMPK) in C2C12 myoblast cells according to FIG. 2A.

As shown in FIGS. 2A-2B, when compared with the control group (denoted as CON in FIGS. 2A-2B), C2C12 cells treated with insulin (100 nM) and AnK (1, 5, 10 and 25 μg/mL) exhibited enhanced protein expressions of membrane GLUT4. The expression ratios of phospho-Akt (p-Akt) to total-Akt (t-Akt) and phospho-AMPK (p-AMPK) to total-AMPK (t-AMPK) were higher in the insulin-treated and AnK-treated cells than in CON group. In FIG. 2B, all values are means±SE; *** $P<0.001$ was compared with the CON group. Furthermore, treatment of AnK (between 1 and 25 μg/mL) was found to be non-toxic to C2C12 cells in the MTT (3-[4,5-dimethylthiazol-2-yl]-2,5-diphenyltetrazolium bromide) assay (data not shown). The results indicate that AnK can enhance expression levels of muscular membrane GLUT4, phospho-Akt, and phosphor-AMPK in vitro, suggesting that AnK has the potential to stimulate muscular glucose uptake and exerts an antidiabetic effect partly by insulin pathway and partly by AMPK activation.

EXAMPLE 2

2.1 AnK Reduces Body Weight Gain and Weights of Adipose Tissue

To verify the antidiabetic and antihyperlipidemic effects of AnK, mice fed on HFD for 8 weeks were administered with distilled water, metformin (Metf), fenofibrate (Feno), or various amounts of AnK as previously described and fed on HFD for additional 4 weeks.

Body weight and weights of adipose tissue for the HF group, which was administered with distilled water, and the AnK-treated HFD groups were first examined. At the beginning, the average body weight of all mice was 20.05±0.13 g. At the end of the experiment, as shown in TABLE 2, body weight and body weight gain were markedly enhanced in the HF group than in the CON group. Compared with the HF group, the HF+AnK2, HF+AnK3, and HF+Feno groups exhibited decreased final body weight, and the HF+AnK1, HF+AnK2, HF+AnK3, HF+Feno, and HF+Metf groups exhibited decreased body weight gain. Furthermore, the HF group consumed less food than the CON group, and no difference was found in food intake between the AnK-, Feno-, or Metf-treated groups, suggesting that the weight-reducing effect of AnK was not resulted from less food intake.

According to TABLE 2, the HF group exhibited enhanced absolute weights of epididymal white adipose tissue (EWAT), mesenteric white adipose tissue (MWAT), retroperitoneal white adipose tissue (RWAT), and visceral fat when compared with the CON group. However, treatment with AnK1, AnK2, AnK3, Feno, or Metf significantly reduced the weights of epididymal, mesenteric, and retroperitoneal white adipose tissues, and the weights of visceral fat. It was noted that Feno-treated mice showed a decrease in brown adipose tissue (BAT) weights, but increased the weights of liver. These results indicate that AnK can reduce body weight gain and weights of adipose tissue and visceral fat at the dose of at least 10 mg/kg body weight/day.

TABLE 2

Effects of AnK on absolute tissue weight, food intake, and liver lipids

| | CON | HF | HF + AnK1 | HF + AnK2 |
|---|---|---|---|---|
| | | Dose (mg/kg/day) | | |
| | | | 10 | 20 |
| Absolute tissue weight (g) | | | | |
| EWAT | 0.531 ± 0.052 | 1.264 ± 0.147### | 0.867 ± 0.065** | 0.841 ± 0.062** |
| MWAT | 0.278 ± 0.031 | 0.439 ± 0.025### | 0.349 ± 0.020* | 0.340 ± 0.013* |
| RWAT | 0.166 ± 0.021 | 0.483 ± 0.064### | 0.323 ± 0.039* | 0.339 ± 0.031* |
| Visceral fat | 0.697 ± 0.056 | 1.747 ± 0.208### | 1.190 ± 0.093** | 1.180 ± 0.106** |
| Skeletal muscle | 0.308 ± 0.014 | 0.412 ± 0.045 | 0.395 ± 0.036 | 0.364 ± 0.022 |
| BAT | 0.158 ± 0.004 | 0.224 ± 0.022# | 0.178 ± 0.007 | 0.172 ± 0.010 |
| Liver (g) | 1.003 ± 0.024 | 0.987 ± 0.029 | 0.946 ± 0.030 | 0.888 ± 0.019 |
| Spleen (g) | 0.099 ± 0.006 | 0.094 ± 0.004 | 0.090 ± 0.003 | 0.085 ± 0.003 |
| Final body weight (g) | 27.21 ± 0.47 | 30.43 ± 1.02# | 28.30 ± 0.61 | 27.55 ± 0.72* |
| Weight gain (g) | 1.61 ± 0.15 | 3.42 ± 0.24# | 1.39 ± 0.81* | 0.70 ± 0.86** |
| Food intake (g/day/mouse) | 2.34 ± 0.04 | 1.99 ± 0.04### | 1.95 ± 0.05 | 1.92 ± 0.07 |
| Liver lipids | | | | |
| total lipid (mg/g) | 53.7 ± 2.7 | 95.9 ± 6.4### | 73.1 ± 4.7*** | 66.0 ± 4.8** |
| triacylglycerol (μmol/g) | 40.6 ± 3.9 | 79.3 ± 6.3### | 56.3 ± 4.2** | 45.7 ± 3.9*** |

| | HF + AnK3 | HF + Feno | HF + Metf |
|---|---|---|---|
| | Dose (mg/kg/day) | | |
| | 40 | 250 | 300 |
| Absolute tissue weight (g) | | | |
| EWAT | 0.809 ± 0.058*** | 0.603 ± 0.041*** | 0.813 ± 0.064*** |
| MWAT | 0.332 ± 0.025* | 0.247 ± 0.025*** | 0.270 ± 0.018*** |
| RWAT | 0.306 ± 0.040* | 0.181 ± 0.020*** | 0.298 ± 0.027** |
| Visceral fat | 1.154 ± 0.096*** | 0.784 ± 0.052*** | 1.111 ± 0.077*** |
| Skeletal muscle | 0.364 ± 0.028 | 0.428 ± 0.026 | 0.380 ± 0.025 |
| BAT | 0.175 ± 0.008 | 0.157 ± 0.013* | 0.220 ± 0.025 |
| Liver (g) | 0.883 ± 0.018 | 1.700 ± 0.070*** | 0.908 ± 0.031 |
| Spleen (g) | 0.104 ± 0.007 | 0.084 ± 0.005 | 0.093 ± 0.006 |
| Final body weight (g) | 27.48 ± 0.46* | 27.55 ± 0.84* | 27.86 ± 0.72 |
| Weight gain (g) | 0.58 ± 0.35** | 0.57 ± 0.55*** | 0.92 ± 0.08** |
| Food intake (g/day/mouse) | 1.98 ± 0.04 | 1.99 ± 0.06 | 1.89 ± 0.04 |
| Liver lipids | | | |
| total lipid (mg/g) | 64.5 ± 5.2** | 64.9 ± 5.1** | 65.3 ± 4.9** |
| triacylglycerol (μmol/g) | 45.2 ± 4.6*** | 47.3 ± 4.6*** | 45.4 ± 4.2*** |

All values are means ± SE (n = 9);
$P < 0.05$ and ###$P < 0.001$ were compared with the CON group;
*$P < 0.05$, $P < 0.01$, and *$P < 0.001$ were compared with the HF group; visceral fat represented the sum of EWAT and RWAT; skeletal muscle included quadriceps muscle, which contains four parts, rectus femoris, vastus intermedius, vastus lateralis, and vastus medialis.

2.2 AnK Reduces Blood Levels of Glucose, Triglycerides, Total Cholesterol, Insulin, and Leptin but Increases Blood Levels of Adiponectin Blood parameters including fasting blood glucose levels for the HF group and the AnK-treated HFD groups were examined and shown in FIGS. 3A-3G to verify the glucose- and insulin-lowering effects of AnK. In FIGS. 3A-3G; all values are means±SE (n=9); ##$P<0.01$ and ###$P<0.001$ were compared with the CON group; * $P<0.05$,  $P<0.01$, and * $P<0.001$ were compared with the HF group.

Figure 3A:
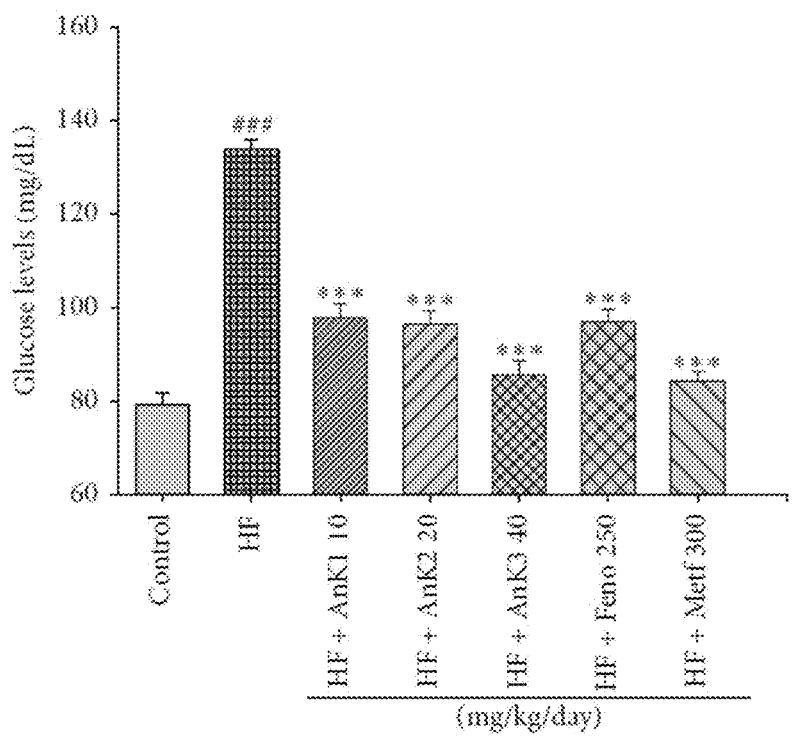
FIGS. 3A-3G show the effects of AnK on blood levels of glucose (FIG. 3A), triglycerides (FIG. 3B), total cholesterol (FIG. 3C), insulin (FIG. 3D), leptin (FIG. 3E), adiponectin (FIG. 3F), and free fatty acid (FFA) (FIG. 3G), respectively, at week 12 in mice fed on low-fat diet and treated with vehicle (control) or fed on high-fat diet and treated with vehicle (HF), various amounts of AnK (HF+AnK1 10 mg/kg/day, HF+AnK2 20 mg/kg/day, and HF+AnK3 40 mg/kg/day), fenofibrate (HF+Feno 250 mg/kg/day), or metformin (HF+Metf 300 mg/kg/day)

As shown in FIG. 3A, the HF group exhibited higher blood glucose levels than the CON group, but treatment with AnK1, AnK2, AnK3, Feno, or Metf significantly reduced blood glucose levels of the HFD-induced mice. AnK administered at 10, 20, and 40 mg/kg body weight/day lowered the blood glucose levels by 26.8-36.0%. The glucose-lowering effect of AnK at the dose of 40 mg/kg body weight/day was comparable to that of metformin, which was given at a dose about seven-fold higher than the dose of AnK.

Figure 3B:
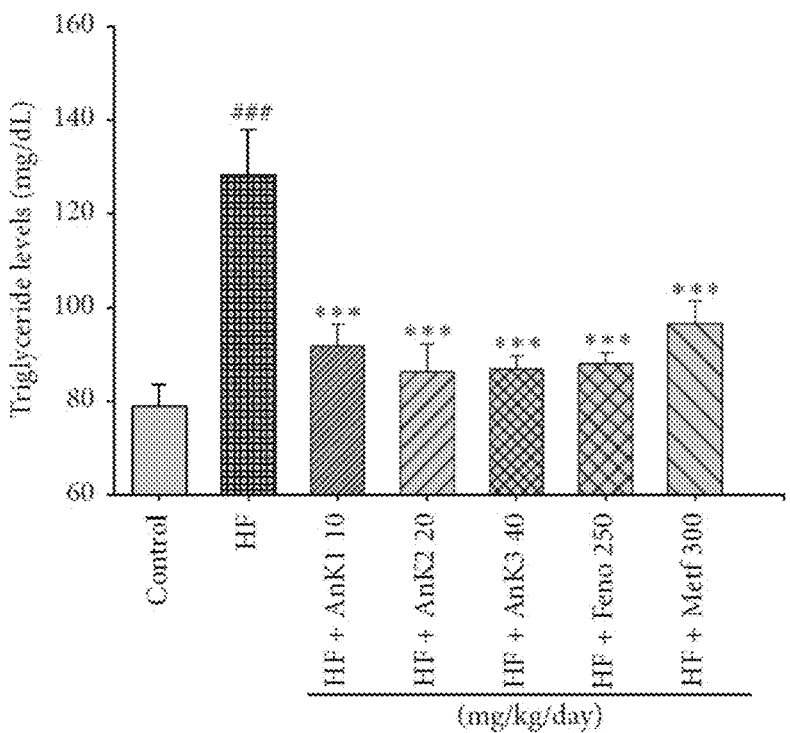
Figure 3C:
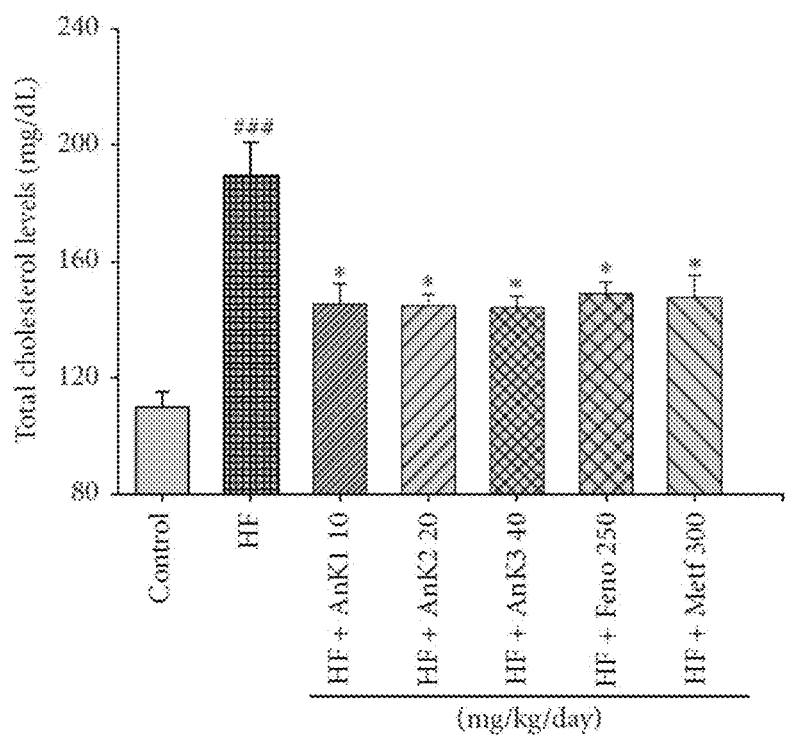
Figure 3D:
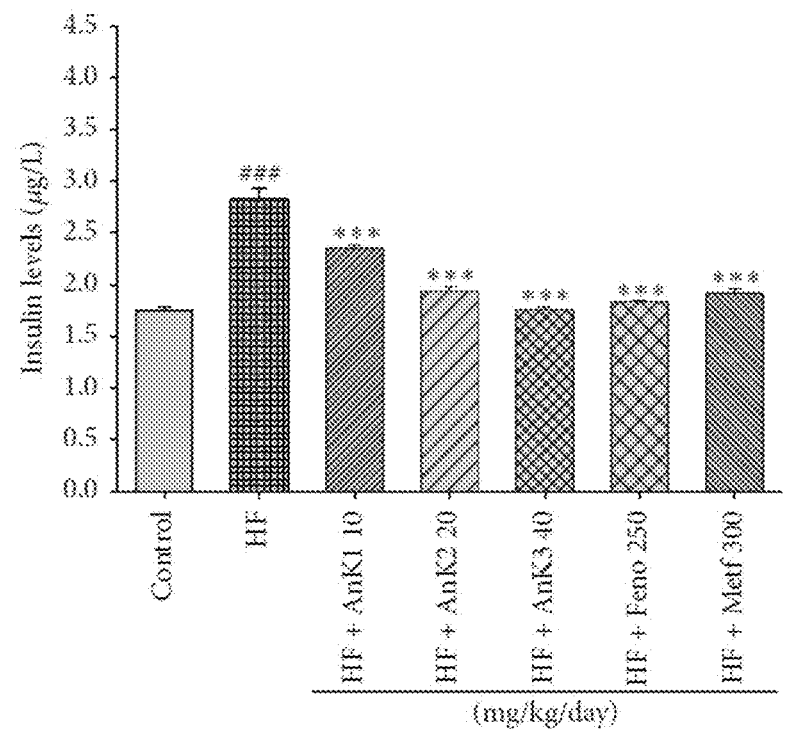
Figure 3E:
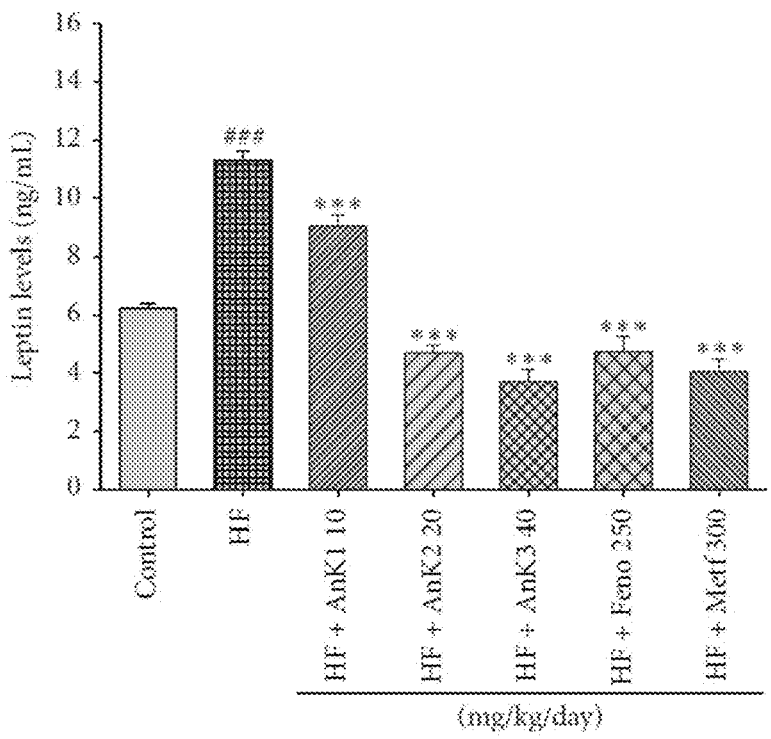
Figure 3F:
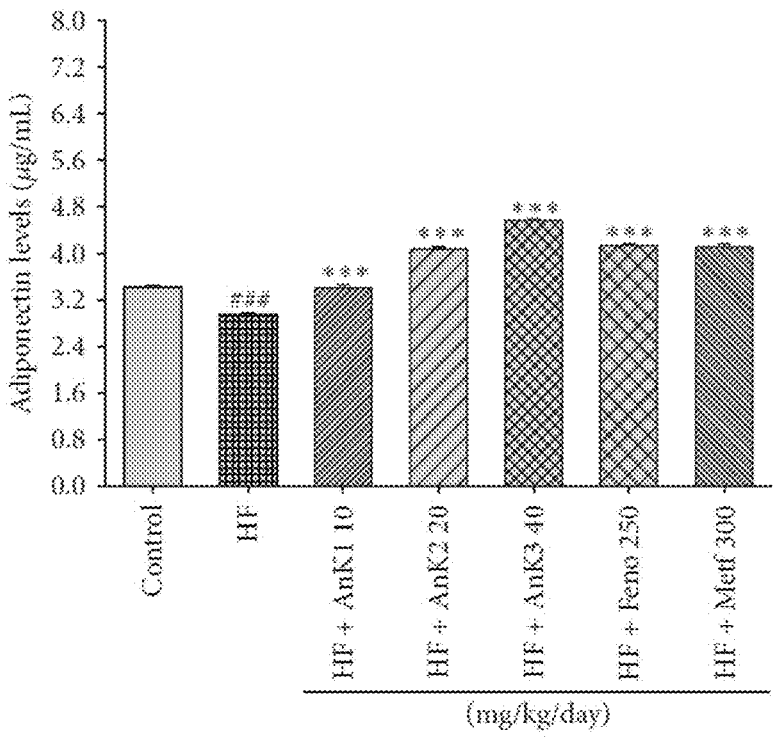
Figure 3G:
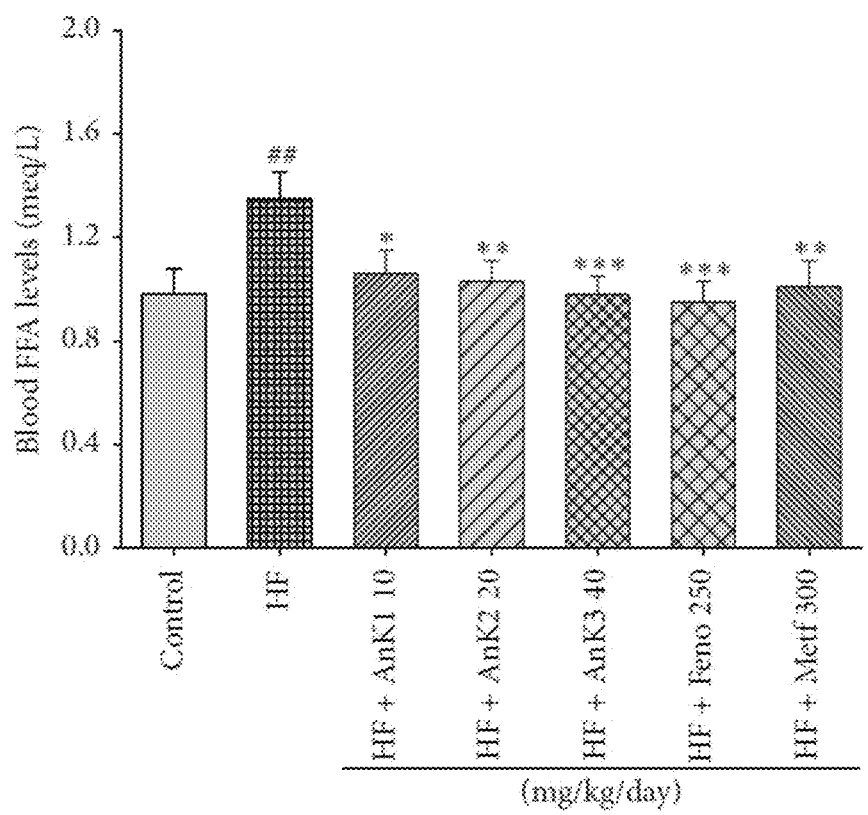

Moreover, as shown in FIGS. 3B-3C and 3G, HFD increased the levels of circulating triglycerides (TG), total cholesterol (TC), and free fatty acid (FFA) in the HF group, whereas the HF+AnK1, HF+AnK2, HF+AnK3, HF+Feno, and HF+Metf groups displayed decreased TG, TC, and FFA levels. The AnK treatment decreased circulating TG by 28.5-32.8%, comparable to the TG-lowering effect of fenofibrate.

In addition, as shown in FIGS. 3D-3F, plasma insulin and leptin levels were higher, but adiponectin levels were lower in the HF group than in the CON group. However, treatment with AnK1, AnK2, AnK3, Feno, and Metf effectively reduced levels of blood insulin, leptin, and FFA, but markedly enhanced adiponectin levels.

Furthermore, according to TABLE 2, the HF group exhibited increased levels of hepatic total lipids and triacylglycerol when compared with the CON group, while the HF+TT1, HF+TT2, HF+TT3, HF+Feno, and HF+Metf groups exhibited significantly decreased levels of hepatic total lipids and triacylglycerol.

These results indicate that AnK can effectively reduce blood levels of glucose, insulin, and leptin, ameliorate hyperglycemia and hyperinsulinemia, and provide protection against HFD-induced insulin resistance. The increased blood levels of adiponectin following AnK administration indicates that AnK can provide a improve insulin sensitivity, because it has been reported that High levels of adiponectin can predict enhanced insulin sensitivity of both glucose and lipid metabolism. The results also indicate that the AnK can reduce blood levels of triglycerides, total cholesterol, and free fatty acids and hepatic levels of total lipids and triacylglycerol, leading to amelioration of hepatic steatosis and hyperlipidemia, including hypertriglyceridemia and hypercholesterolemia.

EXAMPLE 3

Inhibition of Adipocyte Hypertrophy and Hepatocellular Ballooning

Adipocyte hypertrophy, the pathological enlargement of adipocytes, is often found in subjects with type 2 diabetes and hyperlipidemia. To verify the therapeutic effect of AnK on adipocyte hypertrophy, morphology of the epididymal white adipose tissue from mice of the HF group and the AnK-treated HFD groups was examined. Micrographs (magnification 200X) of the EWAT sections for each group were shown in FIG. 4 and analyzed to determine the mean area of an epididymal adipocyte.

Figure 4A:
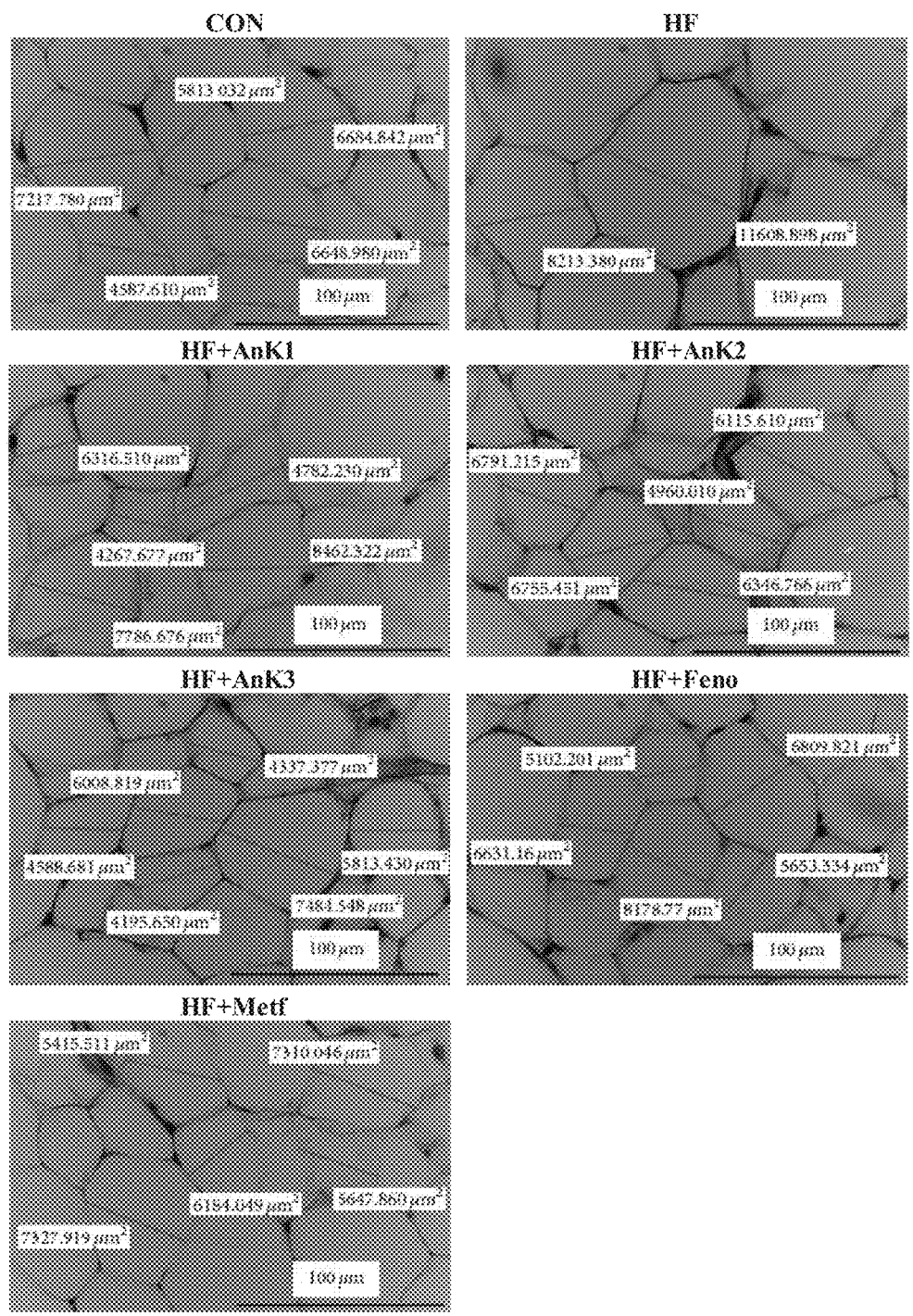
FIG. 4A shows histological micrographs (magnification: 200×) and the mean area ($µm^2$) of adipocytes from the epididymal white adipose tissue of mice of the following groups: CON, HF, HF+AnK1, HF+AnK2, HF+AnK3, HF+Feno, and HF+Metf; the scale bar represents 100 µm.

According to FIG. 4A, adipocyte hypertrophy was observed in the HF group in comparison to the CON group. The mean areas of the adipocytes in the HF group and the CON group were 10142.9±428.1 $\mu m^2$ and 6044.4±359.1 $\mu m^2$, respectively. As shown in TABLE 3, treatment with AnK1, AnK2, AnK3, Feno, or Metf resulted in less adipocyte hypertrophy. These data indicate that AnK inhibits adipocyte hypertrophy and lipid accumulation.

TABLE 3

Effects of AnK on adipocyte hypertrophy

| Groups | Adipocyte size ($\mu m^2$) |
|---|---|
| HF + AnK1 | 6548.6 ± 214.7 |
| HF + AnK2 | 6483.8 ± 319.8 |
| HF + AnK3 | 5670.8 ± 281.6 |
| HF + Feno | 6304.2 ± 316.9 |
| HF + Metf | 5873.7 ± 345.1 |

Hepatocellular ballooning, which is resulted from hepatocyte death and glycogen accumulation in the cell, is usually observed in type 2 diabetes- and hyperlipidemia-related fatty liver or hepatic steatosis. To further validate the therapeutic effect of AnK on this ballooning degeneration, morphology of the liver tissue from mice of the HF group and the AnK-treated HFD groups was examined.

Figure 4B:
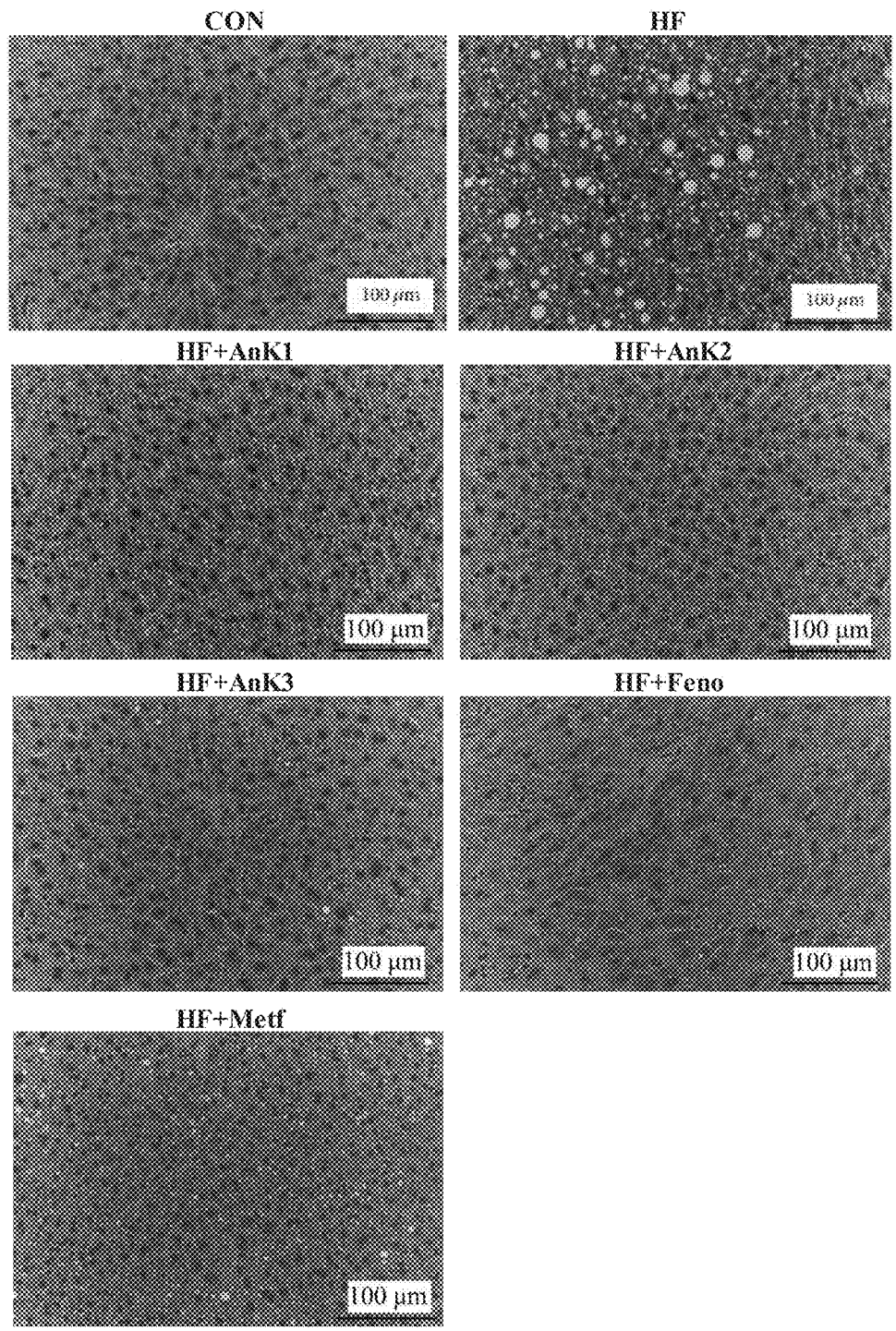
FIG. 4B shows histological micrographs (magnification: 200×) of liver tissue of mice of the following groups: CON, HF, HF+AnK1, HF+AnK2, HF+AnK3, HF+Feno, and HF+Metf; the scale bar represents 100 µm.

As shown in FIG. 4B, when compared with the CON group, the HF group displayed significant ballooning degeneration of hepatocytes, with the nucleolus being squeezed into the side, which is the so-called ballooning. On the basis of previous study, the degree of hepatocellular ballooning is defined in TABLE 4:

TABLE 4

| Grade 0 | Grade 1 | Grade 2 |
|---|---|---|
| Absence of degeneration | Degeneration in a few cells | Degeneration in many cells |

As shown in FIG. 4B and TABLE 5, while HFD induced ballooning, the degree of ballooning was decreased in the HF+AnK1, HF+AnK2, HF+AnK3, HF+Feno, and HF+Metf groups. These data demonstrate that AnK inhibits hepatocellular ballooning.

TABLE 5

Effect of AnK on hepatocellular ballooning

| Groups | Mean score |
|---|---|
| CON | 0 |
| HF | 1.9 ± 0.1 |
| HF + AnK1 | 0.7 ± 0.2 |
| HF + AnK2 | 0.5 ± 0.2 |
| HF + AnK3 | 0.4 ± 0.2 |
| HF + Feno | 0.5 ± 0.1 |
| HF + Metf | 0.7 ± 0.2 |

EXAMPLE 4

Regulation of mRNA Expression of Hepatic Genes Involved in Glucose and Lipid Metabolism The ability of AnK to regulate expression of the following protains essential in glucose and lipid metabolism was further studied. Glucose-6-phosphatase (G6Pase) is a rate-limiting enzyme in gluconeogenesis. Diacylglycerol O-acyltransferase 2 (DGAT2) plays a role in the final step of triglyceride synthesis. PPARα involves in fatty acid oxidation. Adipocyte protein 2 (aP2) is a lipogenic enzyme whose deficiency resulted in protection from the development of dyslipidemia, hyperglycemia, insulin resistance, and fatty liver disease. Increase in apolipoprotein CIII (apoCIII) levels is found to induce the development of hypertriglyceridemia. Sterol regulatory element-binding protein 1c (SREBP1c) is a key lipogenic transcription factor and stimulates lipogenic enzyme expression. Sterol regulatory element-binding protein 2 (SREBP2) is associated with total cholesterol synthesis. To investigate the effects of AnK on gene expression of G6Pase, DGAT2, PPARα, SREBP1c, aP2, apoCIII, and SREBP2 in liver, quantification of the mRNA levels of these proteins from mouse liver of the HF group and the AnK-treated HFD groups was performed.

Figure 5A:
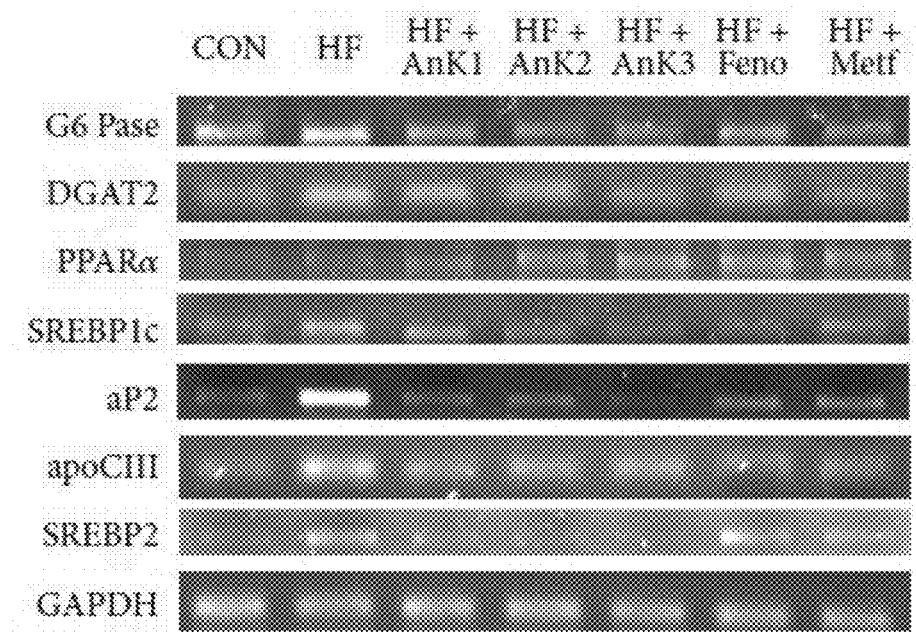
FIG. 5A shows gel images of electrophoresis for semi-quantative RT-PCR analysis of G6Pase, DGAT2, PPARα, SREBP1c, adipocyte protein 2 (aP2), apolipoprotein CIII (apoCIII), and SREBP2 mRNA expression levels in liver tissue of mice of the following groups: CON, HF, HF+AnK1, HF+AnK2, HF+AnK3, HF+Feno, and HF+Metf.
Figure 5B:
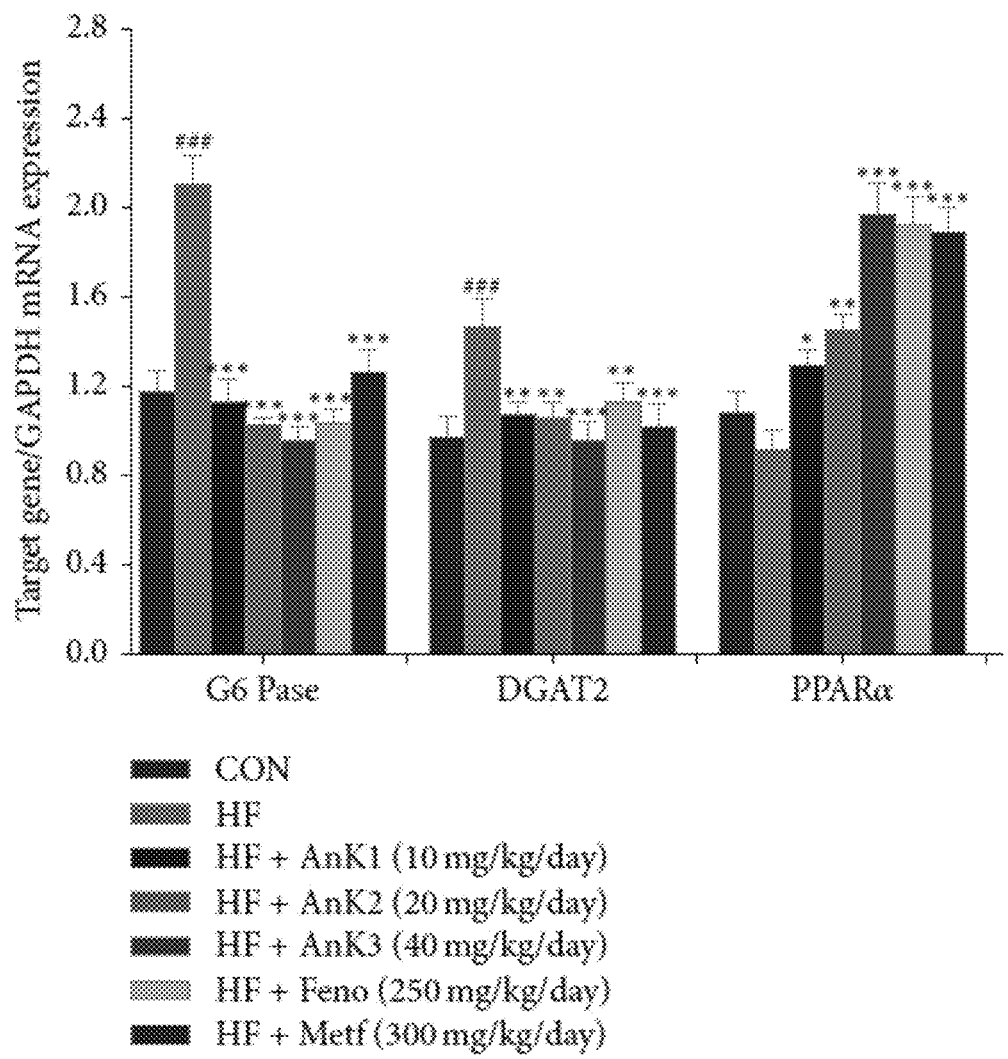
FIG. 5B shows quantification of mRNA expression levels of target genes, including G6Pase, DGAT2, and PPARα, with the values being normalized to GAPDH levels according to FIG. 5A.
Figure 5C:
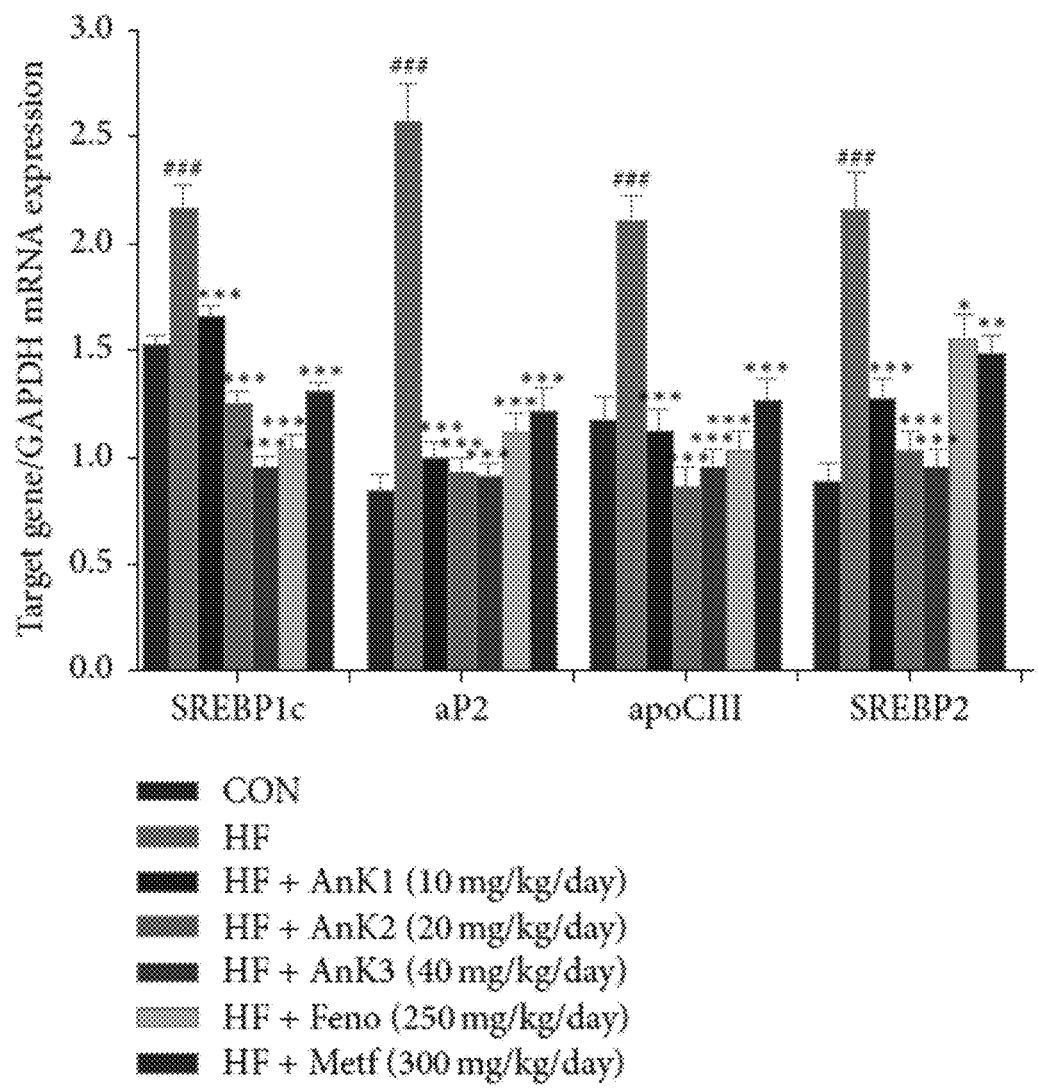
FIG. 5C shows quantification of mRNA expression levels of target genes, including SREBP1c, aP2, apoCIII, and SREBP2, with the values being normalized to GAPDH levels according to FIG. 5A.

As shown in FIGS. 5A-5C, when compared with the CON group, the HF group had higher mRNA levels of G6Pase, DGAT2, SREBP-1c, aP2, apoCIII, and SREBP2, but lower PPARα mRNA levels. However, the HF+AnK1, HF+AnK2, HF+AnK3, HF+Feno, and HF+Metf groups exhibited significantly decreased mRNA levels of G6Pase, DGAT2, SREBP1c, aP2, apoCIII, and SREBP2, but increased PPARα mRNA levels. In FIGS. 5B-5C, all values are means±SE (n=9); ###$P<0.001$ was compared with the CON group; * $P<0.05$,  $P<0.01$, and * $P<0.001$ were compared with the HF group. The results indicate that the antidiabetic and antihyperlipidemic effects of AnK may be resulted from the inhibited expression of G6Pase, which is related to hepatic glucoses production, the inhibited expression of DGAT2, SREBP-1c, aP2, apoCIII, and SREBP2, which are related to lipid synthesis, and the enhanced expression of PPARα, which is related to fatty acid oxidation.

EXAMPLE 5

Regulation of Membrane GLUT4 Expression and Protein Phosphorylation of AMPK and Akt in Skeletal Muscle and Liver GLUT4 expressed at the plasma membrane involves in glucose uptake in skeletal muscle and thus regulates glucose levels in blood. Protein kinase B (often termed Akt) has been reported to stimulate glucose uptake by influencing GLUT4 in skeletal muscle and contributes to suppression of gluconeogenesis in liver. AMPK regulates metabolism of glucose and lipid and its activity depends on phosphorylation of the amino acid residue Thr 172 of the α subunit. To analyze the effects of AnK on GLUT4 expression at the plasma membrane in skeletal muscle and phosphorylation of AMPK and Akt in liver and skeletal muscle, Western blotting of these proteins from the HF group and the AnK-treated HFD groups was performed.

Figure 6A:
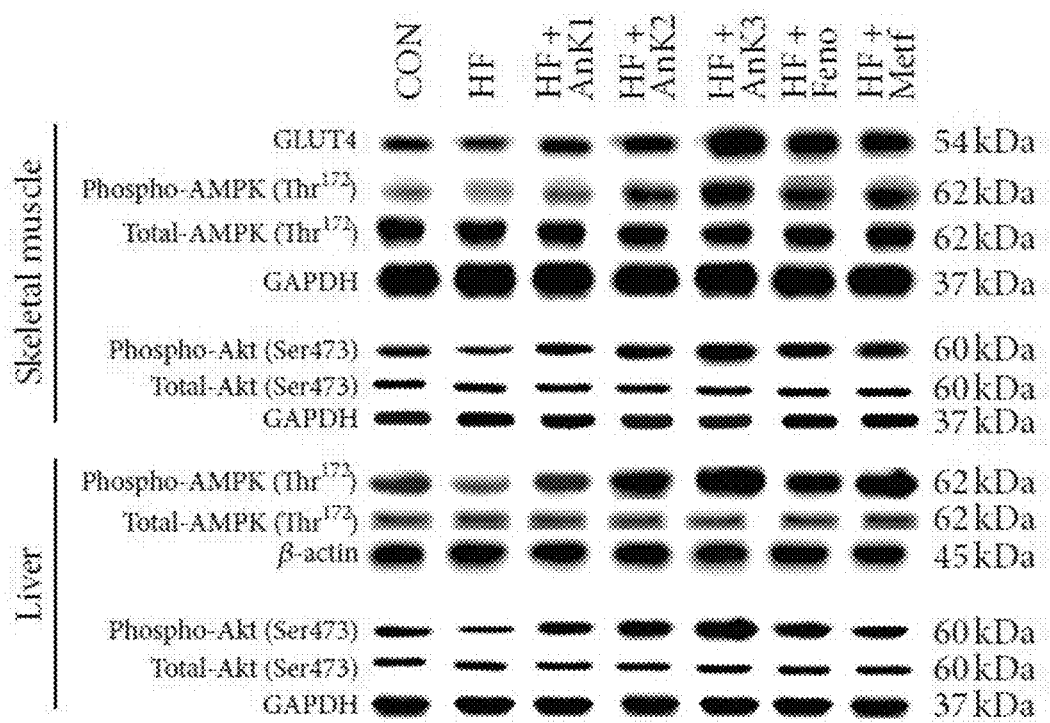
FIG. 6A shows Western blotting images of membrane GLUT4 from skeletal muscle, phospho-AMPK ($Thr^{172}$), total-AMPK, phospho-Akt ($Ser^{473}$), and total-Akt from skeletal muscle and liver tissue of mice of the following groups: CON, HF, HF+AnK1, HF+AnK2, HF+AnK3, HF+Feno, and HF+Metf.
Figure 6B:
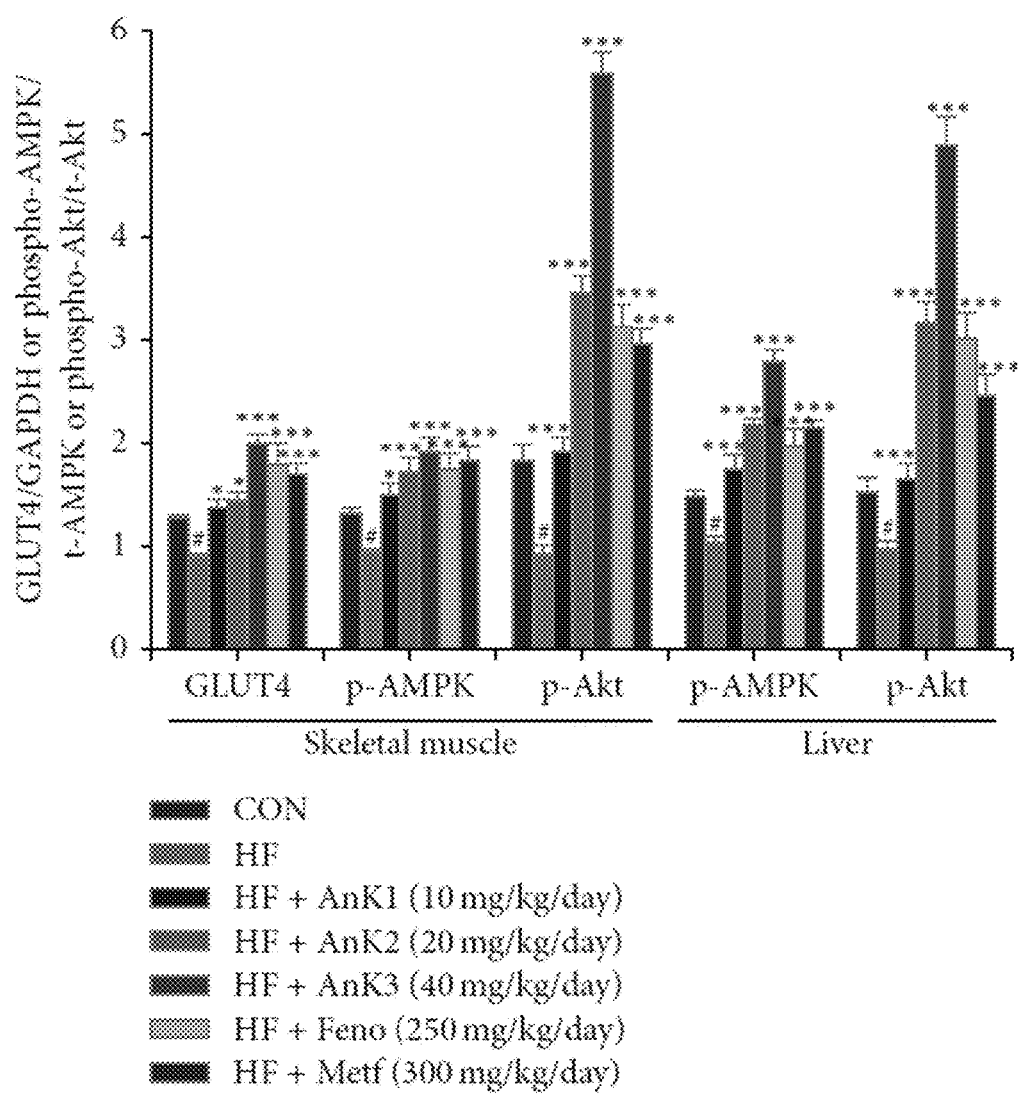
FIG. 6B shows quantification of protein expression levels of membrane GLUT4, normalized to GAPDH levels, and the ratios of phospho-AMPK (p-AMPK) to total-AMPK (t-AMPK) and phospho-Akt (pAkt) to total-Akt (t-Akt) according to FIG. 6A.

As shown in FIGS. 6A-6B, HFD induced decreases in protein expression levels of skeletal muscular membrane GLUT4 in the HF group in comparison to the CON group, while treatment with AnK1, AnK2, AnK3, Feno, or Metf significantly enhanced membrane GLUT4 expression. More specifically, treatment with AnK, Feno, and Metf significantly increased membrane GLUT4 levels by 1.52-2.20-fold, 1.98-fold, and 1.86-fold, respectively, as compared with the HF group. The HF group also exhibited decreased expression levels of phospho-AMPK/total-AMPK (t-AMPK) and phosphor-Akt/total-Akt (t-Akt) in skeletal muscle and liver, whereas these reductions were significantly reversed in the HF+AnK1, HF+AnK2, HF+AnK3, HF+Feno, and HF+Metf groups. In FIG. 6B, all values are means±SE (n=9); #$P<0.05$ was compared with the CON group; * $P<0.05$ and *** $P<0.001$ were compared with the HF group. The results indicate that AnK can stimulate glucose uptake via membrane translocation of GLUT4 and activation of Akt and AMPK, which supports the antidiabetic effect of AnK.

EXAMPLE 6

Regulation of Expression Levels of Target Proteins Involved in Lipid Metabolism in Liver and Adipose Tissue PPARα has been reported to be associated with fatty acid oxidation. Instead, fatty acid synthase (FAS) catalyzes fatty acid synthesis. PPARγ, which is highly expressed in adipocytes, is the master regulator of adipocyte differentiation and lipid accumulation. To investigate the effects of AnK on expression levels of PPARα and FAS in liver and PPARγ anf FAS in adipose tissues, Western blotting of these proteins from the HF group and the AnK-treated HFD groups was performed.

Figure 7A:
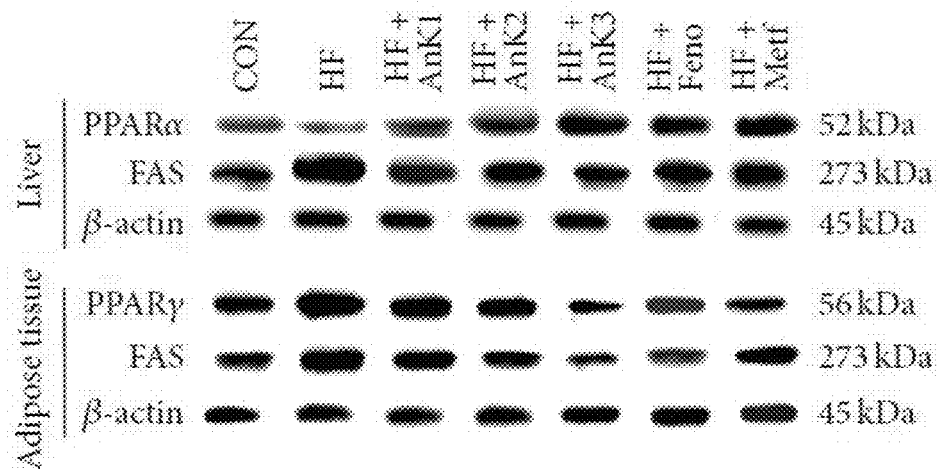
FIG. 7A shows Western blotting images of PPARα from liver and FAS and PPARγ from liver and adipose tissue of mice of the following groups: CON, HF, HF+AnK1, HF+AnK2, HF+AnK3, HF+Feno, and HF+Metf.
Figure 7B:
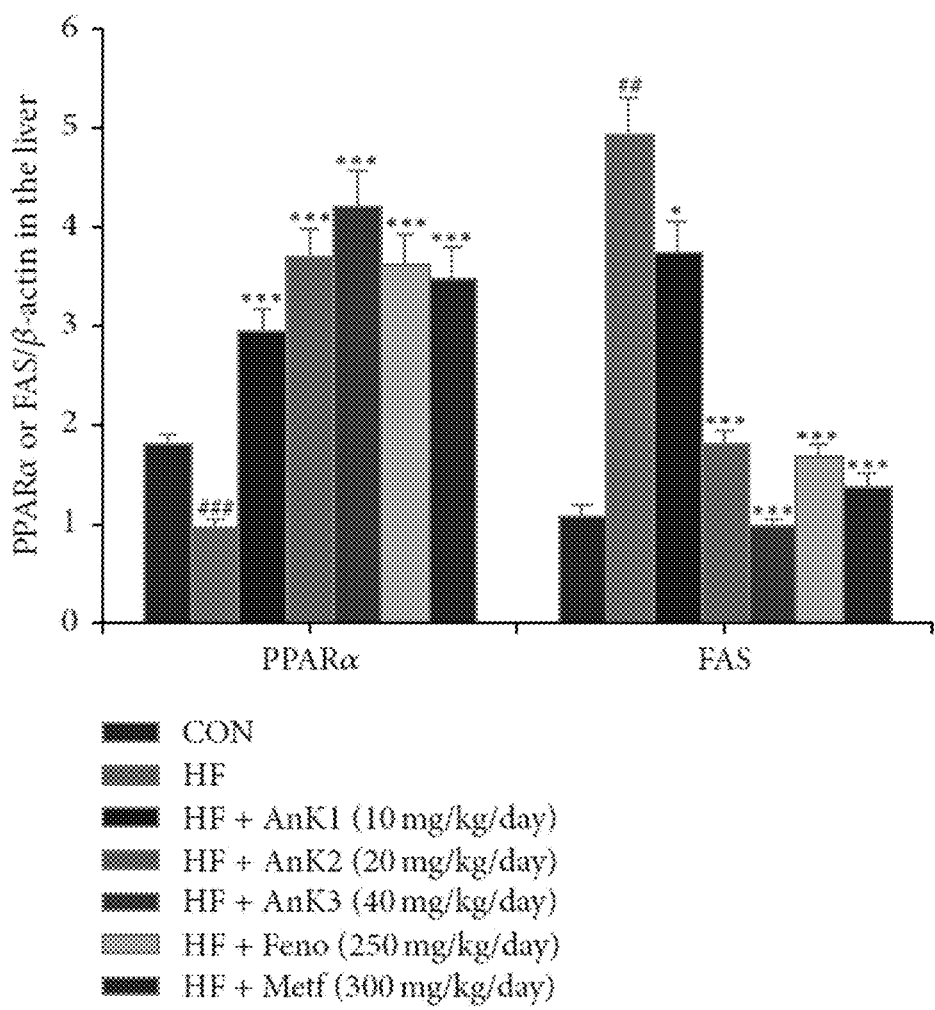
FIG. 7B shows quantification of protein expression levels of PPARα and FAS, normalized to β-actin levels, in liver according to FIG. 7A.
Figure 7C:
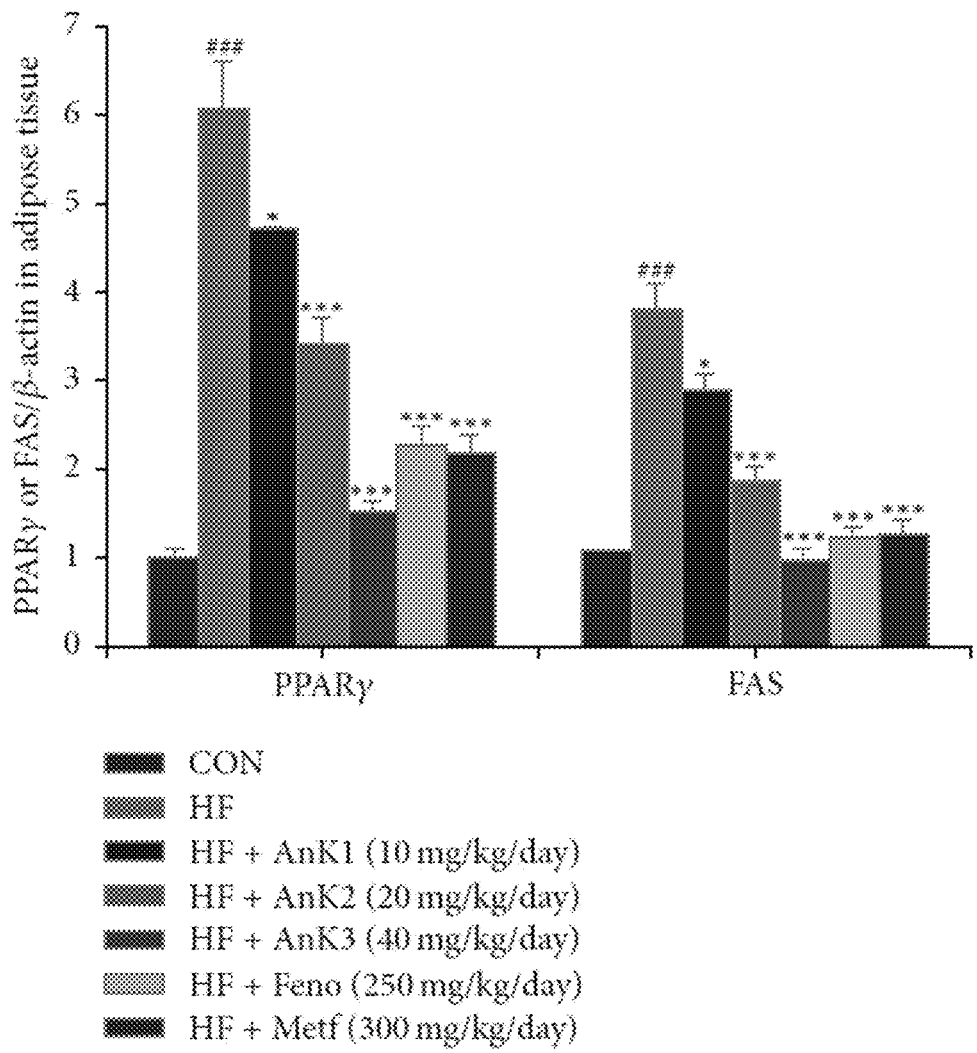
FIG. 7C shows quantification of protein expression levels of PPARγ and FAS, normalized to β-actin levels, in adipose tissue according to FIG. 7A.

As shown in FIGS. 7A-7B, the HF group had decreased PPARα expression but increased FAS expression in liver when compared with the CON group, while treatments with AnK1, AnK2, AnK3, Feno, or Metf significantly increased PPARα but decreased FAS expression levels in liver. Moreover, according to FIGS. 7A and 7C, the HF group had enhanced PPARγ and FAS expressions in adipose tissue when compared with the CON group, while the expression levels of PPARγ and FAS were significantly reduced in the HF+AnK1, HF+AnK2, HF+AnK3, HF+Feno, and HF+Metf groups. In FIGS. 7B-7C, all values are means±SE (n=9); ##$P<0.01$ and ###$P<0.001$ were compared with the CON group; * $P<0.05$ and *** $P<0.001$ were compared with the HF group. The results indicate that AnK exerts the lipid-lowering effect through enhancing hepatic PPARα expression and suppressing FAS and PPARγ expressions.

In conclusion, the present invention provides a method of treating metabolic diseases including type 2 diabetes, insulin resistance, hyperlipidemia, obesity, hyperinsulinemia, and hepatic steatosis by administration of a therapeutically effective amount of AnK to the subjects in need. After the HFD-induced diabetic mice were orally given AnK, significant reductions in blood levels of triglycerides, total cholesterol, free fatty acids, glucose, insulin, and leptin were observed AnK also inhibits adipocyte hypertrophy and ballooning degeneration in liver tissue. The blood glucose-lowering effect of AnK may be attributed to the increased glucose uptake by skeletal muscle due to the enhanced muscular membrane GLUT4 expression, the increased protein expression ratio of phospho-AMPK to total AMPK in skeletal muscle and liver, and the inhibited hepatic gluconeogenesis due to the reduced mRNA expression of G6Pase in liver. The lipid-lowering effect of AnK may be contributed by the reduced production of triglycerides and total cholesterol in liver due to the decreased mRNA expression of DGAT2 and SREBP-1c and the decreased FAS protein expression, the reduced total cholesterol synthesis in liver due to the decreased SREBP2 mRNA expression, and the enhanced fatty acid oxidation in liver due to the increased mRNA expression of PPARα. Furthermore, administration of AnK inhibits lipogenesis in adipose tissue through down-regulation of FAS and PPARγ protein expression, leading to less adipocyte differentiation and fat accumulation.

What is claimed is:

1. A method of treating a metabolic disease in a subject in need thereof, comprising administering to the subject a therapeutically effective amount of antcin K, wherein the metabolic disease is selected from the group consisting of type 2 diabetes, insulin resistance, hyperglycemia, hyperlipidemia, obesity, hepatic steatosis, hyperinsulinemia, and combinations thereof.

2. The method of claim 1, wherein the antcin K reduces blood glucose and blood insulin, and increases insulin sensitivity.

3. The method of claim 2, wherein the antcin K enhances protein expression of membrane glucose transporter type 4 (GLUT4) in skeletal muscle and protein expression ratio of phospho-5' adenosine monophosphate-activated protein kinase (phospho-AMPK) to total AMPK in skeletal muscle and liver, and inhibits mRNA expression of glucose-6-phosphatase (G6Pase) to reduce blood glucose.

4. The method of claim 2, wherein the antcin K increases phosphorylation of protein kinase B (Akt) in skeletal muscle.

5. The method of claim 1, wherein the antcin K reduces triglycerides, total cholesterol, and free fatty acid (FFA) in blood.

6. The method of claim 5, wherein the antcin K inhibits protein expression of fatty acid synthase (FAS) and mRNA expression of sterol regulatory element-binding protein 1c (SREBP1c) and diacylglycerol O-acyltransferase 2 (DGAT2) whereas enhances protein expression of peroxisome proliferator-activated receptor a (PPARα) to promote fatty acid oxidation in liver to reduce triglycerides in blood.

7. The method of claim 5, wherein the antcin K inhibits mRNA expression of sterol regulatory element-binding protein 2 (SREBP2) to reduce total cholesterol in blood.

8. The method of claim 1, wherein the antcin K inhibits hepatocellular ballooning or reduces hepatic total lipids and triacylglycerol.

9. The method of claim 8, wherein the antcin K enhances protein expression of PPARα and inhibits protein expression of FAS to reduce hepatic total lipids and triacylglycerol.

10. The method of claim 1, wherein the antcin K inhibits protein expression of FAS and PPARγ in adipocytes to inhibit adipocyte differentiation and fat accumulation to decrease adipocyte size.

11. The method of claim 1, wherein the antcin K decrease visceral fat mass but increase blood adiponectin to ameliorate the metabolic disease.

12. The method of claim 1, wherein antcin K reduces body weight gain and body weight of the subject.

13. The method of claim 1, wherein antcin K reduces blood leptin.

* * * * *